US006852501B2

(12) United States Patent
White

(10) Patent No.: US 6,852,501 B2
(45) Date of Patent: Feb. 8, 2005

(54) METHODS FOR DETERMINING ATPASE ACTIVITY AND USES THEREOF

(75) Inventor: Peter White, Montreal (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 249 days.

(21) Appl. No.: 10/041,522

(22) Filed: Oct. 24, 2001

(65) Prior Publication Data

US 2002/0102626 A1 Aug. 1, 2002

Related U.S. Application Data

(62) Division of application No. 09/595,833, filed on Jun. 16, 2000, now Pat. No. 6,492,181.
(60) Provisional application No. 60/139,629, filed on Jun. 17, 1999.

(51) Int. Cl.[7] .................................................. C12Q 1/48
(52) U.S. Cl. .......................................... 435/15; 435/18
(58) Field of Search ........................... 435/15, 18, 183, 435/194; 436/103

(56) References Cited

U.S. PATENT DOCUMENTS

| 4,568,649 A | 2/1986 | Bertoglio-Matte | |
|---|---|---|---|
| 6,410,254 B1 * | 6/2002 | Finer et al. | ..................... 435/21 |
| 6,492,181 B1 * | 12/2002 | White | ......................... 436/103 |

FOREIGN PATENT DOCUMENTS

| JP | 1-101899 | * | 4/1989 |
| JP | 4-360700 | * | 12/1992 |
| WO | WO 99/57283 A1 | | 7/1992 |

OTHER PUBLICATIONS

Ekblad E. Determination of Inorganic Orthophosphate From Biological Material in the Presence of Ficoll. Analytical Biochem 83(2)694–702, 1977.*
Chan K. A Direct Colorimetric Assay for Ca+2 Stimulated ATPase Activity. Analytical Biochem 157(2)375–380, 1986.*
Moslen, M. T. et al: "A Stable Colorimetric Assay to Measure Toxin Elevation of Inorganic Phosphate in Bile" Analytical Biochemistry 1988, 168:405–410.
Gonzalez–Romo, P. et al: "A Modified Colorimetric Method for the Determination of Orthophosphate in the Presence of High ATP Concentrations" Analytical Biochemistry 1992, 200:235–238.
Rieger, C. E. et al: "A Continuous Spectrophotometric Assay for Aspartate Transcarbamylase and ATPases" Analytical Biochemistry 1997, 246:86–95.
Zimmerman, S. B. et al: "Deoxycytidine Di– and Triphosphate Cleavage by an Enzyme Formed in Bacteriophage––Infected *Excherichia coli*" The Journal of Biological Chemistry 1961, 236(5); 1480–1486.

Matson, S.W. et al: "DNA Helicases" Annu. Rev. Biochem. 1990, 59:289–329.
Ohnishi, S. et al: "Separation of Phosphomolybdate by Affinity Chromatography", Jornal of Solid–Phase Biochemistry, 1976, 1(4):287–295.
Ohnishi, S.: "A New Method of Separating Inorganic Orthophosphate from Phosphoric Esters and Anhydrides by an Immobilized Catalyst Column", Analytical Biochemistry 1978, 86:201–213.
Bronnikov, G. E. et al.: "Microquantitative Determination of P1–ATP and ADP–ATP Exchange Kinetics Using ThinLayer Chromatography of Silica Gel" Analytical Biochemistry 1983, 131:69–74.
Hergenrother, P. J. et al: "Determination of the Kinetic Parameters for Phospholipase C (*Bacillus cerecus*) on Different Phospholipid Substrates Using a Chromogenic Assay Based on the Quantitation of Inorganic Phosphate" Analytical Biochemistry 1997, 251:45–49.
Yoshimura, K. et al: "Microdetermination of Phosphate in Water by Gel–Phase Colorimetry with Molybdenum Blue" Anal. Chem. 1986, 58:591–594.
Hart, H. E. et al: "Scintillation–Proximity Assay of Antigen–Antibody Binding Kinetics: Concise Communication" J. Nucl Med 1979, 20:1062–1065.
Hart, E.H. et al: "Scintillation Proximity Assay (SPA)–A New Method of Immunoassay" Molecular Immunology 1978, 16:265–267.
Howley, Peter M.: "Papillomavirinae: The Viruses and Their Replication" Fields Virology, 1996 3:2045–2076.
Reimann, Erwin M. et al; Selective Precipaitation of 32Pi onto Filter Papers Application to ATPase and Cyclic Amp Phosphodiesterase Determination; Biochimica et Biophysica Acta 1978 vol. 523 pp. 516–521; Elsevier/North Holland Biomedical Press.
Seals, Jonathan R. et al; A Sensitive and Precise Isotopic Assay of ATPase Activity; Analytical Biochemistry 1978 vol. 90 pp. 785–795; Academic Press.

* cited by examiner

*Primary Examiner*—Ralph Gitomer
(74) *Attorney, Agent, or Firm*—Michael P. Morris; Susan K. Pocchiari; MaryEllen M. Devlin

(57) ABSTRACT

The present invention uses the principle that phosphomolybdate binds to hydrophobic surfaces to isolate the phosphomolybdate complex from other phosphate-containing molecules and further uses the SPA concept to bring a radiolabeled phosphomolybdate complex in close contact with a scintillant for measurement by scintillation counting. Generally, the present invention provides an assay for detecting and measuring the amount of orthophosphate (Pi) in an aqueous reaction mixture, wherein the amount of Pi released is separated from the reaction mixture by: adding a solution of molybdate to the reaction mixture to form a phosphomolybdate complex; and contacting the phosphomolybdate complex with a hydrophobic surface, wherein the surface is capable of being separated from the aqueous reaction mixture to allow measurement of the Pi. Particularly, this invention provides an assay for measuring the ATPase activity of enzymes, more particularly, the HPV E1 helicase.

21 Claims, 14 Drawing Sheets

* denotes current standard conditions

ATPASE SPA ASSAY

```
File    : HPV-11 E1 Km(ATP) by SPA
Monday 3/27/00  2:38 PM

Enzyme Kinetics (no inhibition)
Simple weighting

[Enzyme]                  =    2000.0000

Reduced Chi squared = 32.78
```

| Variable | Value | Std. Err. |
|---|---|---|
| k cat | 0.2938 | 0.0039 |
| Km | 7.5246 | 0.3179 |

| | S<br>uM ATP | Y<br>pM PO4/sec | Calculated |
|---|---|---|---|
| 1 | 2.0000 | 124.5000 | 123.4063 |
| 2 | 5.0000 | 229.0000 | 234.6171 |
| 3 | 10.0000 | 337.9000 | 335.3552 |
| 4 | 25.0000 | 457.8000 | 451.7319 |
| 5 | 50.0000 | 506.1000 | 510.8212 |

Km(ATP) HPV-11 E1

```
File      : HPV-11 E1 Km(ATP) by TLC
Thursday 2/3/00  2:36 PM

Enzyme Kinetics (no inhibition)
Simple weighting

[Enzyme]               =    2000.0000

Reduced Chi squared = 1990
```

| Variable | Value | Std. Err. |
|---|---|---|
| k cat | 0.2150 | 0.0250 |
| Km | 7.4828 | 3.1815 |

| | S uM ATP | Y pM PO4/sec | Calculated |
|---|---|---|---|
| 1 | 3.0000 | 143.3000 | 123.0456 |
| 2 | 8.0000 | 206.7000 | 222.1581 |
| 3 | 16.0000 | 268.3000 | 292.9486 |
| 4 | 40.0000 | 421.7000 | 362.1969 |
| 5 | 75.0000 | 356.7000 | 390.9479 |

Km(ATP) HPV-11 E1, by TLC

METHODS FOR DETERMINING ATPASE ACTIVITY AND USES THEREOF

This application is a Divisional of U.S. patent application Ser. No. 09/595,833 filed Jun. 16, 2000, now U.S. Pat. No. 6,492,181, and claims the priority benefits of U.S. Provisional Application 60/139,629 filed Jun. 17,1999, the disclosures of which are incorporated by reference in their entireties.

FIELD OF THE INVENTION

The present invention relates to a new ATPase assay. This invention particularly relates to a new method for the detection and measurement of the amount of orthophosphate released by hydrolysis of ATP or any other phosphate containing molecule. More particularly, this invention relates to a new method for the measurement of the ATPase activity of the E1 helicase enzyme from the human papilloma virus (HPV).

BACKGROUND OF THE INVENTION

HPV-associated Disease

The human papillomaviruses (HPVs) are small DNA viruses that infect cells of the cutaneous and mucosal epidermis. Over 80 different HPV genotypes have been characterized. Some types, such as HPV-1, -2, -3, -4 and -10, cause cutaneous lesions known as warts or papillomas. These growths are benign and self-limiting, and are found on the hands and feet of 7–10% of the general population. Of greater medical concern are those HPV types that infect the anogenital tract. These genotypes are designated as either "low-risk" or "high-risk" based on their correlation with malignant progression.

So-called low-risk HPVs are associated with genital warts, or condyloma acuminata. For instance, HPV types 6 and 11 are found in more than 90% of benign genital lesions, and very rarely associated with malignant transformation. However, they nonetheless represent a serious public health problem. Approximately 1% of sexually active adults in the U.S.A. have visible genital warts, but in many more cases the infection is sub-clinical. In fact, an estimated further 15% of people aged 15–49 display molecular evidence of HPV infection, in the form of viral DNA detectable by polymerase chain reaction (PCR) assay. Indeed, HPV is ranked as the most common sexually-transmitted viral agent in the U.S.A. and U.K., and its incidence is increasing steadily.

Infection with high-risk HPV types such as 16, 18, 31 and 33, has been strongly linked to the development of anogenital malignancies, most notably cervical cancer. In fact, HPV types 16 and 18, while rarely found in benign genital lesions, are detectable in about 70% of all invasive carcinomas of the cervix. The link between HPV and anogenital cancer is well documented—recent studies have found that almost 90% of cervical carcinomas contain HPV DNA.

Current Therapies and the Need for a Virus-Specific Treatment

In spite of the pervasiveness of HPV infection and its possibly life-threatening consequences, no virus-specific inhibitor has yet been described. Antiviral drug discovery for HPV has proven quite difficult thus far as a result of difficulties encountered in propagating the virus in the laboratory.

All current therapies for HPV infection rely on the non-specific destruction or removal of infected tissue. Accepted surgical procedures include the use of dry ice, liquid nitrogen, $CO_2$ laser therapy, electrocautery or local excision. Various cytotoxic agents are also used to destroy tissue, such as salicylic acid, tricholoroacetic acid, podophyllin, colchicine, bleomycin and cantharidine.

While the risk of cancer makes these procedures the most prudent for the treatment of high-risk HPVs, less invasive treatments are being sought to manage the low-risk genotypes. Compounds that stimulate the immune system have been investigated with the goal of reproducing the spontaneous regression often seen with benign lesions. Imiquimod, such an immune response modifier, has recently passed clinical trials and been approved for treatment of HPV-associated genital warts.

Patients with genital warts often experience high recurrence rates—usually 30–90%-following non-specific treatments such as surgery. Such poor efficiency is a result of the incomplete elimination of HPV DNA, or the presence of virus in normal-appearing tissue adjacent to the papilloma. Obviously, there is a substantial need for an effective, virus-specific therapy for HPV infection, which has thus far gone unmet.

Viral DNA Replication and E1

Semi-conservative DNA replication is an intricate process mediated by many enzymes and accessory proteins. Helicases are enzymes that function during DNA replication, catalyzing the unwinding of duplex DNA ahead of the replication fork. They are very common in prokaryotic and eukaryotic cells, as well as most viruses. The exact mechanism by which helicases convert the binding and hydrolysis of ATP into mechanical energy to power the unwinding of DNA and their own simultaneous motion along the nucleic acid stand is still not completely understood.

The 72 kDa HPV E1 protein has been classified as a member of helicase superfamily III along with the T antigen of Simian Virus 40 (SV40 TAg), with which it is structurally and functionally homologous. E1 and Tag belong to a noteworthy subgroup of viral DNA helicases which have the ability to recognize and bind specific DNA sequences at the viral origin of replication (ori). Also, while most DNA helicases require a region of single-stranded DNA for entry, these proteins can initiate unwinding from completely double-stranded DNA, provided it contains an ori.

Molecular Events at the HPV Origin of Replication

Human papillomaviruses contain approximately 8 kb of double-stranded circular DNA. In the basal cells of the epidermis, the genome is replicated and maintained extra-chromosomally at a steady-state level of about 20–100 copies per cell. High-level amplification of the genome only occurs once the cell has terminally differentiated and migrated to the upper layers of the epithelium.

In a cell-free DNA replication system, the E1 protein can direct origin-specific DNA replication by itself at sufficient concentrations, when provided with the full complement of host replication proteins including the DNA polymerase $\alpha$ primase enzyme. However, replication is greatly stimulated by the viral E2 protein, and at limiting concentrations of E1 the in vitro replication becomes completely E2-dependent. This is a consequence of E1 having a relatively low affinity for its DNA binding site. E2 helps to localize E1 to the origin by acting as an accessory protein. The E1 and E2 binding sites at the viral ori are in close proximity, falling within about 100 bp of each other. The carboxy terminus of E2 binds its palindromic site on DNA, while the amino terminus binds E1, thus bringing E1 to its binding site.

E1 as a Target for Antiviral Therapy

Recently, pharmaceutical companies have been able to substantially expand and accelerate their antiviral compound screening programs as a consequence of advances in molecular biology. Viruses are now routinely examined at the molecular level to find specific inhibitors of virus-encoded gene products.

For several viruses, enzymes such as polymerases, kinases and proteases have been targets for inhibition. In contrast, of the approximately 8 distinct proteins encoded by the HPV genome, the E1 helicase is the only one with enzymatic activity (Fields et a., 1996, Fields Virology, $3^{rd}$ Ed. Lippincoff-Raven, Philadelphia, Chap. 65 and refs. therein). E1 displays ori-specific DNA-binding activity, E2-binding activity, ATPase activity, and DNA helicase activity—all of which can be assayed independently for potential inhibitors. In addition, it is the most highly conserved of all papillomavirus proteins, so an inhibitor of E1 would likely be effective against multiple HPV types.

High throughput screens are known that allow the discovery of inhibitors of the helicase activity of E1 (WO 99/57283, Nov. 11, 1999). Even though ATP is needed to drive E1 helicase activity and is included in the reaction, this helicase assay cannot be used to identify competitive inhibitors of E1 ATPase function. This is a direct result of very low $K_m$ of the ATPase, for example approximately 10 $\mu$M for HPV-11 E1, and the fact that the helicase assay is routinely run with 300 $\mu$m-1 mM ATP). A more sensitive assay must be developed if the ATP binding site of E1 is to be targeted for inhibition.

Existing ATPase Assays

Helicase activity is virtually always associated with nucleoside triphosphatase activity (Matson et al., Ann. Rev. Biochem., 1990, 59, 289). Enzymatic ATP hydrolysis has been measured by a variety of methods, including colorimetric reactions; in all cases, enzymatic reactions are performed according to enzyme-specific protocols where reaction conditions are not dependent on the detection procedure (except for the inclusion of radiolabeled ATP). The detection procedure differs for the different assays in the following ways:

TLC:

The inclusion of [$\alpha$-$^{33}$P] or [$\gamma$-$^{33}$P] ATP in the substrate for an ATPase reaction results in the release of radiolabeled phosphate or ADP. Because of their different polarity, [$^{33}$P]-labeled ATP, ADP and phosphate can also be separated by thin layer chromatography (Bronnikov et al., Anal. Biochem., 1983, 131, 69) in a running solvent (e.g. lithium chloride/formic acid). The two species migrate at different distances on a TLC plate based on their relative affinities for the polar mobile phase and non-polar solid phase. Results are analyzed by scintillation counting or PhosphorImager analysis.

Although the TLC assay for quantification of released phosphate produces accurate data for ATPase activity and inhibition, it is unsuited for the mass-screening of potential inhibitors. The spotting and running of large numbers of TLC plates is time-consuming and labor-intensive. A method that lends itself to 96-well plate format and rapid quantification is needed if an ATPase assay is to be implemented in HTS format.

Charcoal:

ATP binds to charcoal but orthophosphate does not (Zimmerman et al. J. Biol. Chem. 1961, 236 (5), 1480). Thus if a reaction is run using $\gamma$-labeled ATP and charcoal is added, the starting material is adsorbed, but the product remains in solution. One can run this as a 96-well plate assay by filtering solutions through charcoal-containing filter plates, and counting the flow-through. This is not likely to be highly reproducible, and is not amenable to robotic screening.

Coupled-Enzyme Assays:

There are a number of related procedures in which another reaction is carried out on the phosphate product by a second enzyme (Rieger et al., 1997, Anal. Biochem. 246, 86 & refs. contained therein). These assays are very useful for kinetic studies, because absorbance change is generated continuously over the course of the assay, so that the reaction course can be monitored without removing aliquots as necessary for the other methods above (the distinction between continuous and stop-time assays). These methods are not significantly more sensitive than the molybdate assay (below) however, and screening results would be further complicated by the possibility of false positives being inhibitors of the coupling enzyme.

Molybdate:

Ammonium molybdate forms a complex only with phosphate to form phosphomolybdate. Pyrophosphate, nucleotide triphosphates, or other phosphate-containing molecules resulting from the reaction do not interact with molybdenum oxides. Most of the calorimetric reactions are based the formation of a complex between phosphate and the molybdate ion in acid solution, followed by reduction or binding to dyes that form colored complexes. Many variations to these techniques have been introduced with the goal of increasing sensitivity and color stability, and decreasing the amount of spontaneous ATP hydrolysis that occurs during the color-developing incubation (Gonzalez-Romo et al., Anal. Biochem. 1992, 200, 235). For instance, the phosphomolybdate complex can be reduced by ascorbic acid to generate a blue molybdenum chromogen with maximum absorbance at 700 nm (Hergenrother et al., Anal. Biochem. 1997, 251, 45). Another method is based on the formation of a brilliant green complex with malachite green in an acid medium, which has a maximum absorbance at 650 nm (Moslen et al., Anal. Biochem. 1983, 131, 69).

In fact, the malachite green assay was previously evaluated as a potential test for the ATPase activity of E1, but was found to be unsuitable because it could not accurately detect concentrations of phosphate lower than 25 $\mu$M. This presented a problem, because detection of competitive inhibitors is optimal at substrate concentrations below the $K_m$ of an enzyme. As previously mentioned, the $K_m$ (ATP) of the HPV-11 E1 ATPase has been shown to be about 10 $\mu$M, so the E1 ATPase reaction is routinely carried out at around 1–10 $\mu$M ATP. In addition, substrate consumption in an inhibition experiment is kept below 30%, so that substrate concentration remains essentially constant over the time of the reaction. The result is that 3 $\mu$M is the maximum concentration of phosphate that is released—well below the 25 $\mu$M detection limit of the malachite green assay.

All these calorimetric ATPase assays require a minimum ATP concentration of several hundred micromolar. The value of $K_m$(ATP) for HPV-11 E1 being approximately 10 $\mu$M (measured in the absence of DNA), thus to effectively screen for competitive inhibitors of E1 ATPase activity, one should perform assays using [ATP] <10 $\mu$M.

Adsorption of Phosphomolybdate on Solid Support:

Phosphomolybdate is a large heteropolymolybdate, with a stoichiometry of $[PM_{o12}O_{40}]^{3-}$. Because of its relatively low charge, it can be extracted from aqueous solution into organic solvents or adsorbed onto a hydrophobic surface such as Sephadex beads or nitrocellulose filters. Ohnishi et al. (J. Solid-Phase Biochem. 1976, 1(4), 287) and Ohnishi (Anal. Biochem. 1978, 86, 201) disclose a method for isolating the phosphomolybdate complex from solution by affinity chromatography on polyvinyl polypyrrolidone (PVPP) column. PVPP acts as a catalyst for the complexing reaction between $PO_4$ and molybdenum and thereby selectively adsorbs the complex over other phosphate-containing molecules. Phosphate may be radioactively labeled and eluted from the column for counting of radioactivity. This method is limited by the fact that the labeled phosphate needs to be separated from the reaction mixture before counting. There remains a need for a robust method for phosphate determination that is amenable to a high throughput format.

Yoshimura et al. (Anal. Biochem. 1986, 58, 591) disclose a calorimetric micro-determination of molybdenum-blue by adsorbing the complex on Sephadex gel-phase. This procedure requires reduction of the complex prior to the adsorption and measures the phosphate concentration by direct absortiometry of the heteropoly acid concentrated in the gel phase. This procedure requires separation of the gel beads from the supernatant prior to measurement by colorimetry. Although this calorimetric method allows for detection of low concentrations of phosphate, it remains unsuitable for automation.

Scintillation Proximity Assay:

Hart et al. (Molec. Immunol. 1979, 16, 265) and Hart et al. (J. Nucl. Med. 1979, 20, 1062) disclose a new method for immunoassay called "scintillation proximity assay". This technology used scintillant latex particles coated with a ligand that specifically binds an organic reactant being investigated. All further applications of this technology with hydrophobic beads has relied on providing a specific ligand coated on the beads to bind specifically to a molecule.

U.S. Pat. No. 4,568,649 discloses such beads coated with a specific ligand and specifies that the remaining active sites on the beads must be blocked prior to the assay to prevent the reactant of interest or others from binding directly to the beads rather than to the ligand. This disclosure leads away from the present invention.

Despite the wide applications of this technology since its inception, there has not been the slightest suggestion that this same technology could be used advantageously to detect radiolabeled phosphate through hydrophobic interaction with a phosphomolybdate complex. Applicant's use of the SPA concept in the detection of ATPase activity is founded on the observation that the hydrophobic phosphomolybdate complex binds to hydrophobic surfaces, particularly to the surface of polyvinyl toluene SPA beads, whereas the charged ATP molecule does not. Applicant has used that property to separate the orthophosphate from ATP or ADP and takes advantage of the scintillant-coated beads for measurement of radioactive orthophosphate. Applicant therefore provides a robust method for detecting and measuring orthophosphate. This assay is amenable to large scale and provides reproducible results for detection of Pi in the low nanomolar range. This method is also suitable for kinetic analysis not easily performed by prior art assays.

SUMMARY OF THE INVENTION

The present invention uses the principle that phosphomolybdate binds to hydrophobic surfaces to isolate the phosphomolybdate complex from other phosphate-containing molecules and further uses the SPA concept to bring a radiolabeled phosphomolybdate complex in close contact with a scintillant for measurement by scintillation counting.

In a first embodiment, the present invention provides a method for detecting and measuring radiolabeled orthophosphate (Pi) in an aqueous reaction mixture, comprising the steps of:

a. adding a solution of molybdate to said reaction mixture under acidic conditions to form a phosphomolybdate complex; and b. contacting said phosphomolybdate complex with a scintillant hydrophobic surface;

whereby binding of phosphomolybdate to the surface provides enough proximity for the radiolabeled phosphate to induce measurable scintillation of the scintillant correlating the amount of orthophosphate.

In a second embodiment, the present invention consists of a method for determining ATPase activity, comprising the steps of:

a. mixing radiolabeled [$\gamma$-$^{33}$P]ATP with an ATP hydrolyzing enzyme;

b. incubating reaction mixture a sufficient time to afford orthophosphate to be released from hydrolysis;

c. adding a solution of molybdate to said reaction mixture to form a phosphomolybdate complex;

d. contacting said phosphomolybdate complex with a scintillant hydrophobic surface; and e. measuring scintillation of said scintillant as a means to calculate the amount of said orthophosphate.

Optionally, the method also comprises: step f) adding a solution of CsCl to said reaction mixture prior to counting. Further optionally, the method comprises step g) adding a solution of citric acid to said CsCl-containing mixture prior to counting.

In a third embodiment, the present invention consists of an assay for screening inhibitors of a phosphate-hydrolyzing enzyme activity comprising the steps of: carrying out steps a to e (and optionally steps f and g) according to the method above, in the presence and absence of a candidate inhibitor; and comparing the amounts of orthophosphate in each case to calculate the levels of inhibition.

Commercially available SPA beads are microscopic beads impregnated with scintillant, and are available with a variety of molecules attached to their surface (e.g. streptavidin, glutathione, protein A). Polyvinyl toluene (PVT) SPA beads have relatively hydrophobic surfaces, and are capable of selectively adsorbing phosphomolybdate from reaction mixtures in the presence of excess ATP. Although SPA beads are treated to make them less hydrophobic, the hydrophobic interaction may be enhanced by high concentrations of cesium chloride commonly used to float beads in SPA protocols. In an aqueous medium, weak $\beta$-particle emitters such as [$^{33}$P] need to be in close physical proximity to scintillant molecules to cause them to emit light—otherwise their energy is dissipated and lost in the solvent. Thus, [$^{33}$P]-labeled phosphate complexed with molybdate and bound to the bead surface causes activation of the scintillant, whereas [$^{33}$P]-labeled ATP free in solution does not. The light emitted by a sample is measured by a p scintillation counter and is proportional to the amount of phosphate present. SPA beads are commercially available and are presently treated by the company with a polyhydroxy film to be less hydrophobic. It is however contemplated by the Applicant that non-treated SPA beads may be particularly suitable for this particular assay.

The method and assays of the present invention are useful not only for the HPV E1 helicase, but for any ATPase, NTPase, or any enzyme which generates orthophosphate as a product, especially if the substrate $K_m$ is in the nanomolar to low micromolar range.

Particularly, the assay of the present invention is useful for determining the ATPase activity of various ATP hydrolyzing enzymes where it is desirable to run the assay at nM to low $\mu$M concentrations of substrate. Such enzymes include (without being restricted thereto): helicases (e.g. from other viruses such as HPV, HSV, CMV, HCV), other infectious agents (e.g. bacteria), or cellular helicases; other energy transducing ATPases (such as for example myosins, dyneins, kinesins), ion transport ATPases, or chaperonins; other nucleotide phosphate-hydrolyzing enzymes (e.g. G proteins); protein or small molecule phosphatases; or inorganic pyrophosphatases.

In a fourth embodiment, the present invention comprises a kit for measuring radiolabeled orthophosphate in an aqueous solution, said kit comprising:

a. a solution of molybdate; and b. a scintillant hydrophobic surface;

wherein said molybdate solution is added to said aqueous solution to form a phosphomolybdate complex, said complex being captured by said hydrophobic surface to induce measurable scintillation thereto.

A number of documents are cited in the present application. The content of such citations is incorporated herein by reference.

Other objects, advantages and features of the present invention will become more apparent upon reading of the following non-restrictive description of the preferred embodiments with reference to the accompanying drawings which is exemplary and should not be interpreted as limiting the scope of the invention.

DETAILED DESCRIPTION OF THE PREFERRED EMBODIMENTS

Definitions

Figure 1A:
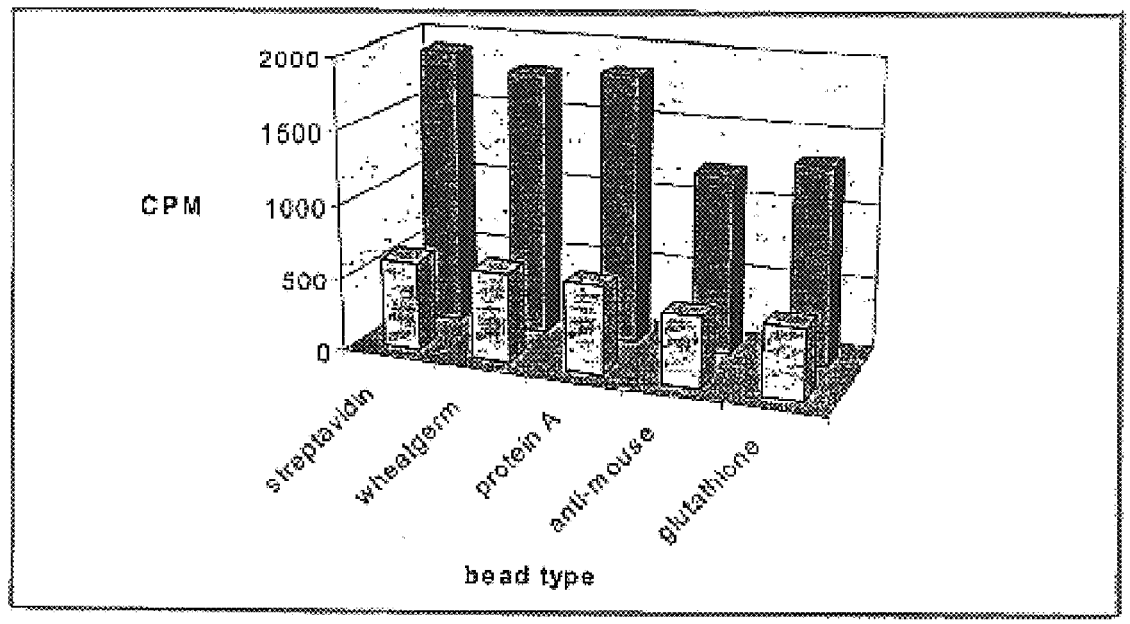
FIG. 1: The effect on SPA signal of using various bead types. (a) cpm for E1 reactions and blanks. (b) control to blank ratio.

The term "scintillant hydrophobic surface" as used herein means a hydrophobic surface that is impregnated, integrated, coated or otherwise contains a scintillant.

The term "scintillant" as used herein means a fluorescent molecule (also called fluorescer) that, when placed in close proximity with radiation energy emitted from a radiolabeled reactant thereto, is activated to emit light energy detectable and measurable by a scintillation counter.

Preferred Embodiments

According to a first embodiment of the present invention, there is provided a method for detecting and measuring radiolabeled orthophosphate (Pi) in an aqueous reaction mixture, comprising the steps of:

a. adding a solution of molybdate to said reaction mixture under acidic conditions to form a phosphomolybdate complex; and b. contacting said phosphomolybdate complex with a scintillant hydrophobic surface; whereby binding of phosphomolybdate to said surface provides enough proximity for the radiolabeled phosphate to induce measurable scintillation of the scintillant correlating the amount of said orthophosphate.

According to second embodiment of the invention, there is provided a method for determining phosphate-hydrolyzing enzyme activity, comprising the steps of:

a. mixing radiolabeled [γ-$^{33}$P]ATP with a said enzyme;

b. incubating reaction mixture a sufficient time to afford orthophosphate to be released from hydrolysis;

c. adding a solution of molybdate to said reaction mixture to form a phosphomolybdate complex;

d. contacting said phosphomolybdate complex with a scintillant hydrophobic surface; and e. measuring scintillation of said scintillant as a means to calculate the amount of said orthophosphate.

Optionally, the method also comprises: step f) adding a solution of CsCl to said reaction mixture prior to counting. Further optionally, the method comprises step g) adding a solution of citric acid to said CsCl-containing mixture prior to counting.

According to a third embodiment of the present invention, there is provided an assay of screening inhibitors of a phosphate-hydrolyzing enzyme activity comprising the steps of: carrying out steps a to e (optionally steps f and g) according to the method described above, in the presence and absence of a candidate inhibitor; and comparing the levels of inhibition.

According to a fourth embodiment of the present invention, there is provided a kit for measuring radiolabeled orthophosphate in an aqueous solution, said kit comprising:

a. a solution of molybdate; and b. a scintillant hydrophobic surface;

wherein said molybdate solution is added to said aqueous solution to form a phosphomolybdate complex, said complex being captured by said hydrophobic surface to induce measurable scintillation thereto.

Preferably, according to the above embodiments of this invention, the molybdate solution and hydrophobic surface may be added simultaneously to the reaction mixture.

Preferably, the embodiments of this invention further comprises the step of: adding a solution of CsCl to the reaction mixture prior to counting. More preferably, the invention further comprises a step of: adding a solution of citric acid to said CsCl-containing mixture prior to counting. Most preferably, the CsCl and citric acid are added simultaneously to the reaction mixture.

Preferably, the reaction mixture containing CsCl and citric acid is incubated for longer than one hour prior to scintillation counting.

Preferably, the ammonium molybdate is at a final concentration of from 0.05% to 0.3%, more preferably from 0.1% to 0.2% w/v. Most preferably, the ammonium molybdate is at a final concentration of about 0.17% w/v.

Preferably, the hydrophobic surface is selected from the group consisting of: polyvinyltoluene (PVT), Sephadex, latex, polystyrene, polyacrylamide, acrylamide, agarose, polypropylene, polycarbonate, and Sepharose. More preferably, the hydrophobic surface is polyvinyl toluene beads such as SPA beads.

Preferably, the CsCl is at a final concentration higher than 1 M. More preferably, the CsCl is at a final concentration ranging from 2M and 4M. Most preferably, the CsCl is at a final concentration of about 3.5M.

Preferably, the citric acid is at a final concentration ranging from 0.05 and 0.2M. More preferably, the citric acid is at a final concentration of about 0.1 M.

Preferably, the phosphate-hydrolyzing enzyme is selected from the group consisting of: helicase, ATPase, and phosphatase. More preferably, the enzyme is an ATPase. Most preferably, the ATPase is the E1 helicase from human papillomavirus.

EXAMPLES

Abbreviations used in the Examples Include:

| | |
|---|---|
| AmMo | ammonium molybdate |
| ATP-γ-S | adenosine-5'-O-(3-thiotriphosphate) |
| cpm | counts per minute |
| DMSO | dimethylsulfoxide |
| DTT | dithiothreitol |
| EDTA | ethylenediaminetetraacetic acid |
| HEPES | N-[2-hydroxyethyl]piperazine-N'-[2-ethane sulfonic acid] |
| MES | 2-[N-morpholino]ethane sulfonic acid |
| MgOAc | magnesium acetate |
| PEI | polyethyleneimine |
| Pi | inorganic orthophosphate |
| PVPP | polyvinylpolypyrrolidone |
| PVT | polyvinyl toluene |
| SPA | scintillation proximity assay |
| TLC | thin-layer chromatography |

Materials and Methods

Polyhistidine-tagged HPV-11 E1 was expressed in baculovirus-infected insect cells and purified by Ni-affinity chromatography as described in WO 99/57283 (incorporated herein by reference).

Example 1

Protocol for ATPase Scintillation Proximity Assay (SPA) using HPV E1

Radiolabeled [γ-$^{33}$P]ATP (NEN) was prepared upon receipt by diluting it 100-fold in the reaction buffer and storing it at −80° C. Material stored in this way was good for greater than one month. E1 ATPase reactions were run in a buffer consisting of 20 mM HEPES, pH 7.5, 0.05 mM EDTA and 1 mM DTT, and 0.05% Igepal CA-630 (equivalent to Nonidet P40). Volumes and concentrations given below are typical, but these can be varied somewhat with minimal effect on results, as shown in later examples. One μM ATP (Amersham Pharmacia) and 500 μM MgOAc were mixed with [γ-$^{33}$P]ATP at 100-fold dilution from the stored material (10,000 dilution from the stock), or approximately 1 nCi/μL when fresh. The actual ATP concentration contributed by [γ-$^{33}$P]ATP was approximately 1 nM; this amount could be reduced further if necessary. Sufficient enzyme was added to give the desired level of conversion. For example, 4 nM HPV-6a E1 converted approximately 30% of the substrate to ADP and phosphate in 2 hours. A typical reaction volume was 40 μL; reactions were run at room temperature in 96-well plates, typically Optiplates (Packard).

At the desired time, 40 μL reactions were stopped by adding 20 PL of a SPA bead-AmMo mixture. This mixture consisted of one part 2% (w/v) AmMo in 2.4M HCl to two parts streptavidin PVT SPA beads (Pharmacia Amersham #RPNQ0007) suspended at 30 mg/mL in 50 mM HEPES plus 0.02% sodium azide. The ammonium-molybdate solution was usually made fresh daily whereas the SPA bead suspension was stable for greater than one month. The mixture can be made several hours in advance, and can even be used for several days when stored at 4° C. Immediately after adding the ammonium molybdate-bead mixture, 80 µL of 7M cesium chloride plus 0.2 M citric acid were added. Plates were shaken briefly and then allowed to sit for greater than one hour. The extent of phosphate production was then determined by scintillation counting using the TopCount (Packard). If desired, cpm can be converted to phosphate concentration by comparison of SPA results to those determined by TLC (see below) for identical reactions. Alternatively, results can be compared to a "100% control", a reaction with a large excess of enzyme previously confirmed by TLC to give complete conversion of ATP to phosphate and ADP. Blanks containing no enzyme but otherwise the same were run in parallel and subtracted.

Example 2

E1 ATPase TLC Assay

ATPase reactions were run just as in the SPA format. At the end of the planned reaction time, reactions were stopped by adding one-half volume of ice-cold 500 mM EDTA, pH 8.0. One to two µL reaction samples were spotted onto polyethyleneimine-coated cellulose TLC plates (Sigma) and eluted in a solution of 1M LiCl and 1M formic acid. [γ-$^{33}$P] phosphate and ATP are determined using the Storm 860 phosphorimaging system (Molecular Dynamics). For each sample, including blanks, the phosphate and ATP spot intensities were quantified and % phosphate was calculated as:

$$100 \times \frac{\text{(phosphate intensity)}}{\text{(phosphate intensity + ATP intensity)}}.$$

Blank values were in the same range as for the SPA, approximately 2–5%, and were subtracted from the values for each reaction to give the value of %-phosphate produced by the enzymatic reaction.

Example 3

Effect of Varying Detection Conditions on Signal and Blank

Many of the reactions in this section were run with slightly different conditions using a reaction buffer of 20 mM MES, pH 7.0, 10% glycerol, and 0.05 mM EDTA. Reactions were run with 10 µM ATP (approximately 1 nM [γ-$^{33}$P]ATP), 500 µM MgOAc, and sufficient E1 to give approximately 20% conversion of substrate in 90 minutes at room temperature. As for examples 1 and 2, reactions were run in Packard Optiplates. In these experiments, detection was typically accomplished by mixing 20 PL of ATPase reaction with 20 µL 2% AmMo in 1.2 M HCl containing 0.05% Tween-20. After 10 minutes, 20 µL of streptavidin SPA bead suspension was added (10 mg/mL in 50 mM HEPES, pH 7.5+0.02% NaN$_3$), after a brief mix this was followed by 20 µL of 7.0 M CsCl. After mixing, plates were allowed to stand for one hour before counting on the TopCount as described in Example 1.

Figure 1B:
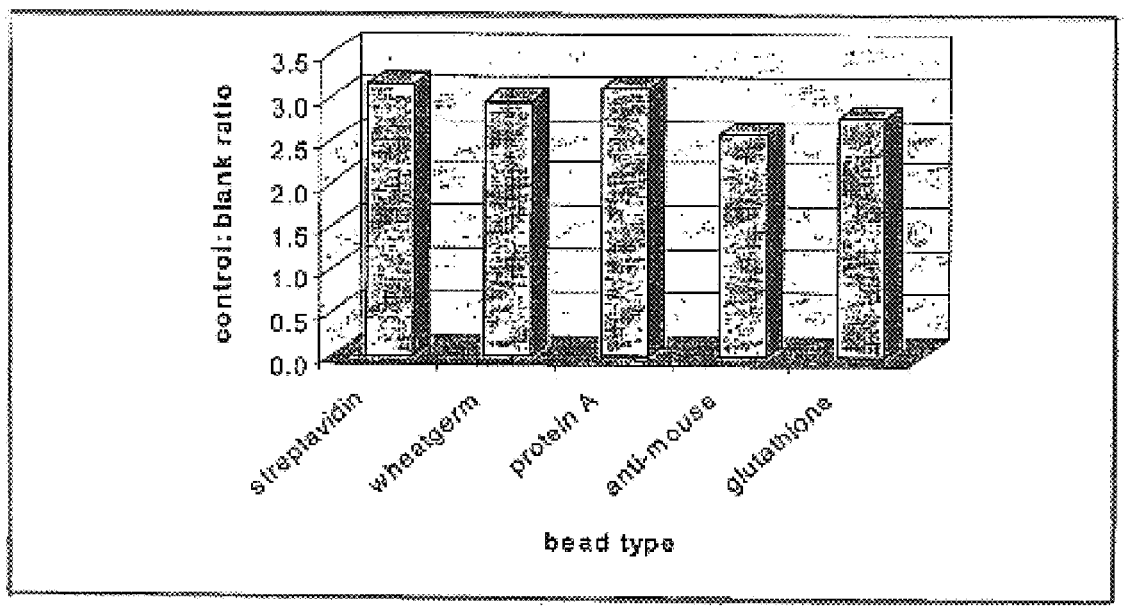

SPA Bead Type:

PVT-SPA beads are available with a variety of molecules attached to their surface. Types that were available for evaluation in the assay included streptavidin, wheat germ agglutinin, protein A, anti-mouse-IgG, and glutathione. Although it is the hydrophobic properties of PVT beads that has affinity for phosphomolybdate, a variety of coatings were tested to see if the type of the molecule on the surface had any effect on the SPA signal. Cpm data are shown in FIG. 1A. The ratios of control signal and blank signal, or "signal-to-background" ratios, are shown in FIG. 1B. There is no significant effect of coating type. Similar results have also been obtained with copper (His-tag-binding) beads, and in fact, uncoated PVT beads, provided by Amersham-Pharmacia, also give an equivalent signal. Yttrium silicate SPA beads do not work in this assay, as expected since they lack a hydrophobic surface.

Figure 2A:
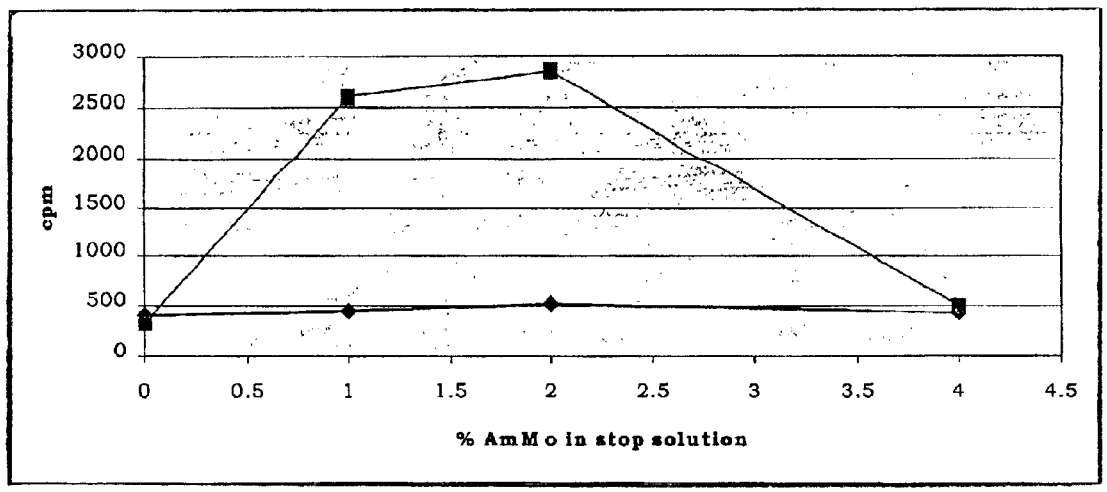
FIG. 2: The effect on SPA signal of varying the AmMo concentration. Concentrations given are % AmMo (w/v) as dissolved in HCl prior to addition to reactions. (a) cpm for E1 reactions (squares) and blanks (diamonds). (b) control to blank ratio.
Figure 2B:
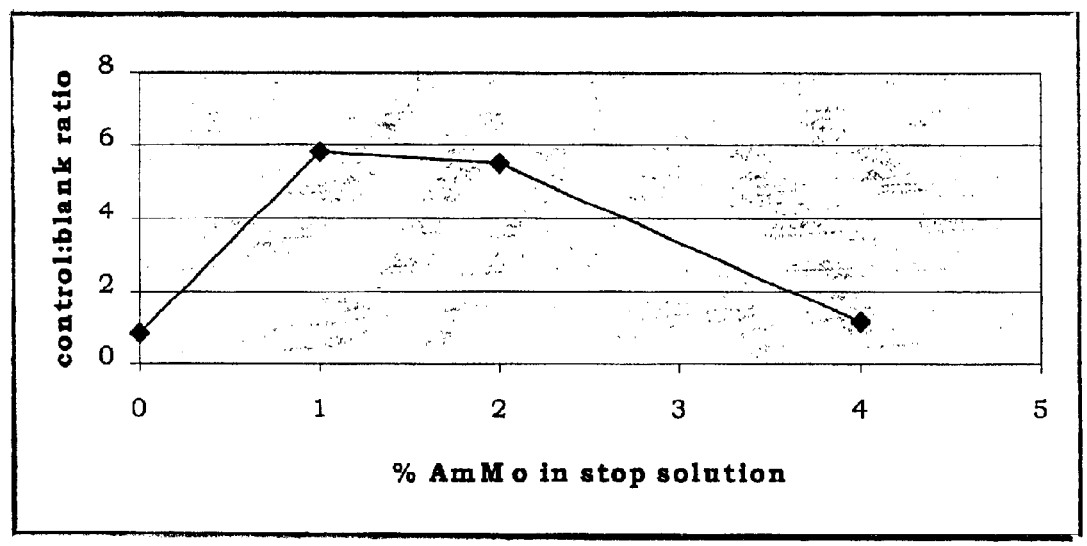

Ammonium Molybdate Concentration:

The function of ammonium molybdate in the stop solution is to complex the released phosphate in the ATPase reaction. The tested concentrations of ammonium molybdate in the stop solution ranged from 1 to 4%. The effects on cpm are shown in FIG. 2A, and signal-to-background ratios are shown in FIG. 2B. [Note: the blank is relatively unaffected by increasing concentrations of AmMo. Thus, under these conditions, the background does not seem to result from contaminating orthophosphate present in the ATP solution, but may rather be due to nonspecific sticking of ATP to the beads or capture of some β-particle radiation emitted by [γ-$^{33}$P]ATP in solution].

Figure 3A:
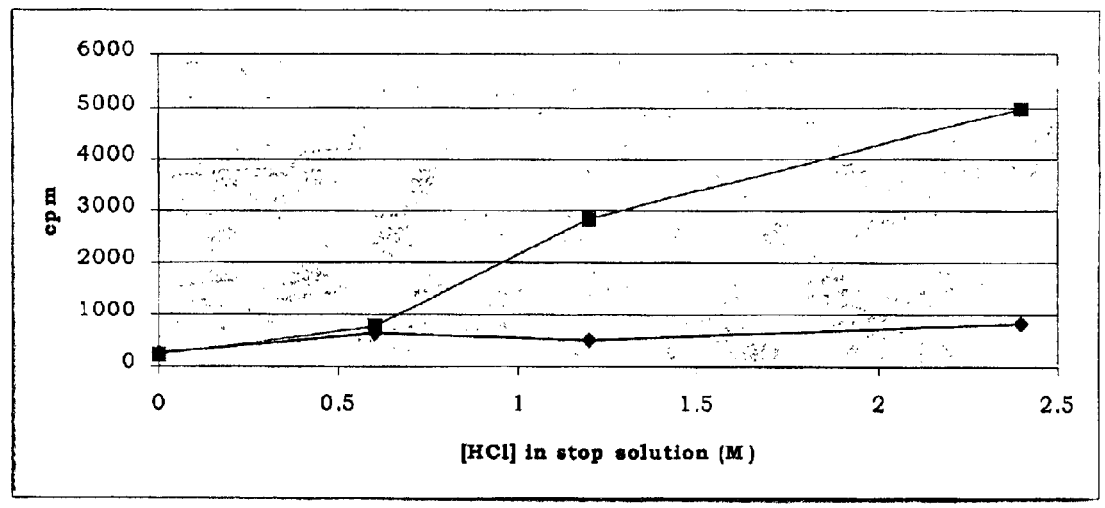
FIG. 3: The effect on SPA signal of varying the HCl concentration in the AmMo solution. (a) cpm for E1 reactions (squares) and blanks (diamonds). (b) control to blank ratio.
Figure 3B:
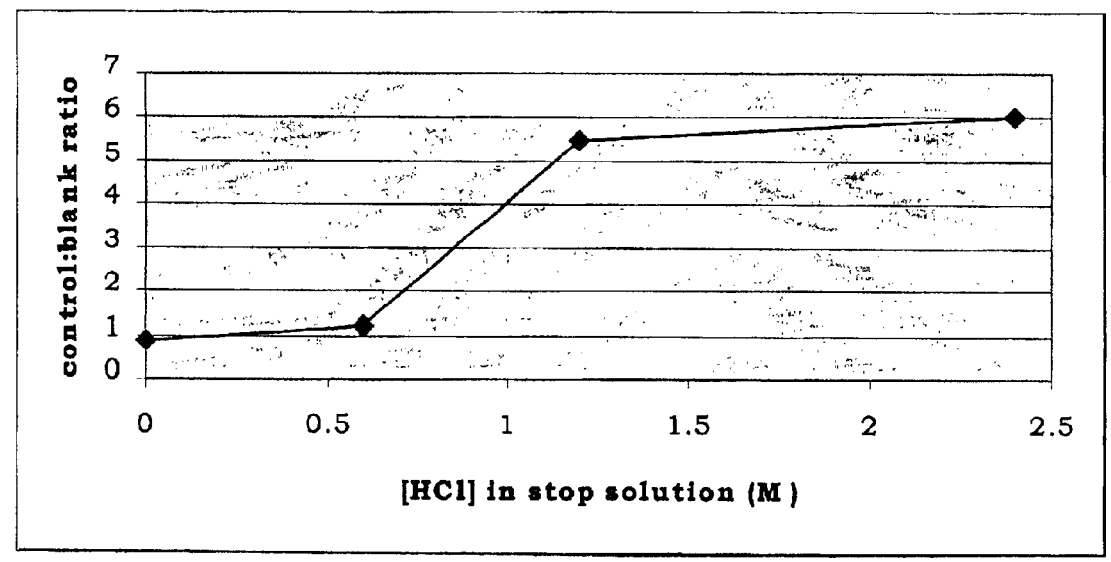

HCl Concentration:

The function of HCl in the stop solution is to provide an acidic medium in which the phosphomolybdate complex can form. The effects on cpm of HCl concentrations ranging from 0 to 2.4 M in the stop solution are shown in FIG. 3A, and signal-to-background ratios are shown in FIG. 3B. Under these conditions, values greater than 1 M were determined to be optimal.

Figure 4A:
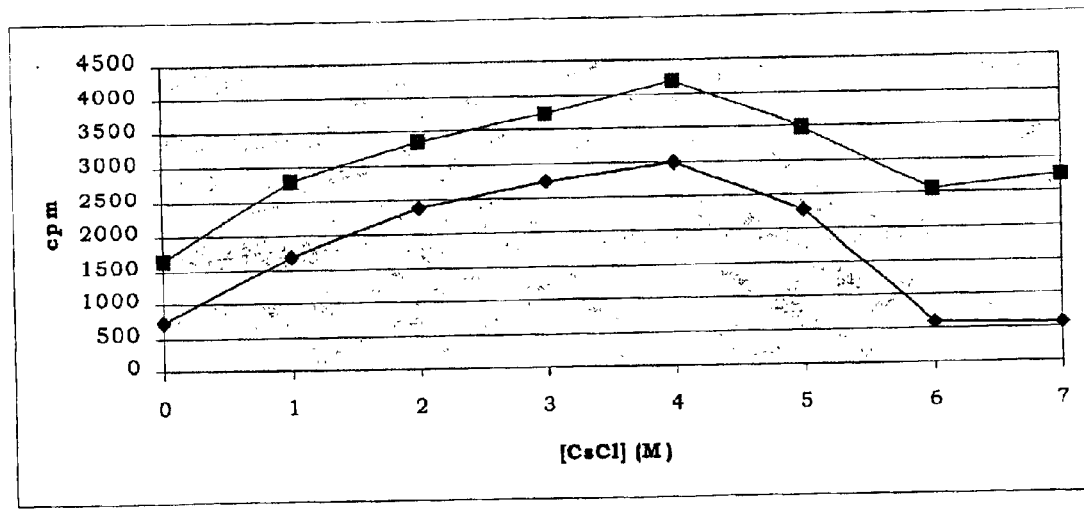
FIG. 4: The effect on SPA signal of varying the CsCl concentration. Concentrations given for the stock solution which was added to reactions as described in Example 3. (a) cpm for E1 reactions (squares) and blanks (diamonds). (b) control to blank ratio.
Figure 4B:
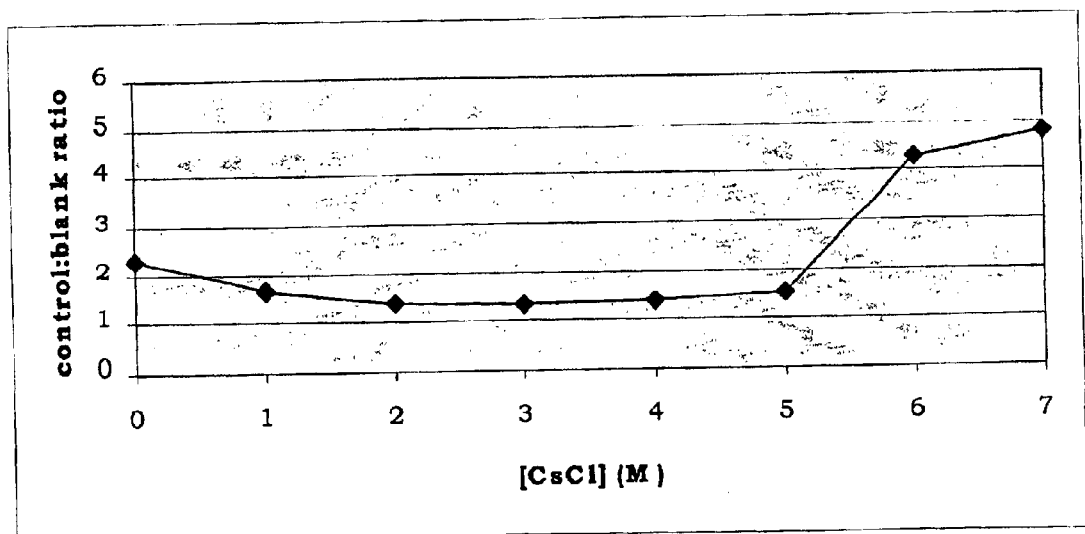

CsCl Concentration:

CsCl is added prior to scintillation counting for two purposes. The first is to produce a high-salt medium that enhances the hydrophobic effect, strengthening the binding of the phosphomolybdate complex to the SPA beads; the second is to increase the density of the fluid in the well. PVT SPA beads have a specific gravity of approximately 1.05 g/mL, and tend to stay dispersed in aqueous solution, settling only slowly to the bottom over several hours. The addition of high-molarity CsCl increases the density of the liquid, causing the SPA beads to form a thin layer floating at the surface, thus increasing the detectable signal. The 7.0 M CsCl is essentially a saturated solution. The effect on cpm of adding 20 µL of CsCl at different concentrations is shown in FIG. 4A, and the effect on signal-to-background ratios is shown in FIG. 4B. Optimum signal to background was obtained using a 7.0 M solution.

Figure 5A:
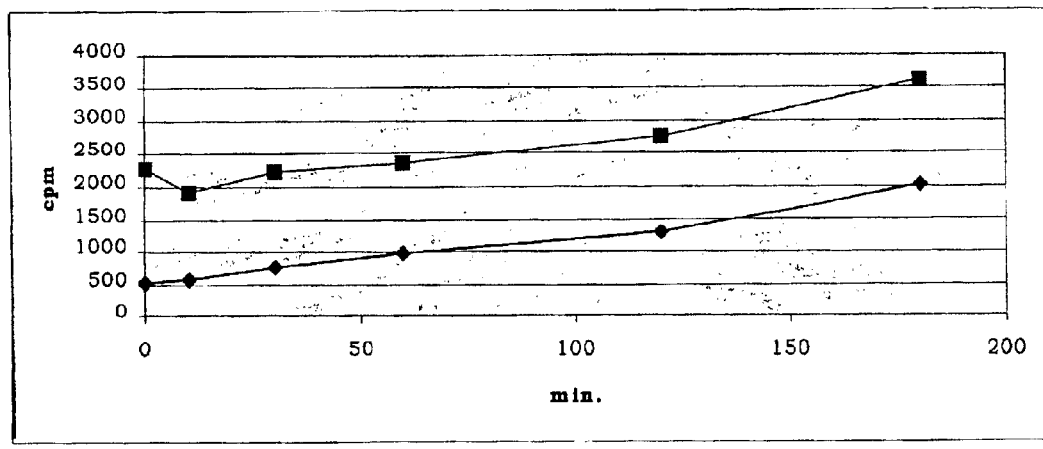
FIG. 5: The effect on SPA signal of varying the time the reaction is incubated with AmMo prior to additions of SPA bead suspension and CsCl. (a) cpm for E1 reactions (squares) and blanks (diamonds). (b) control to blank ratio.
Figure 5B:
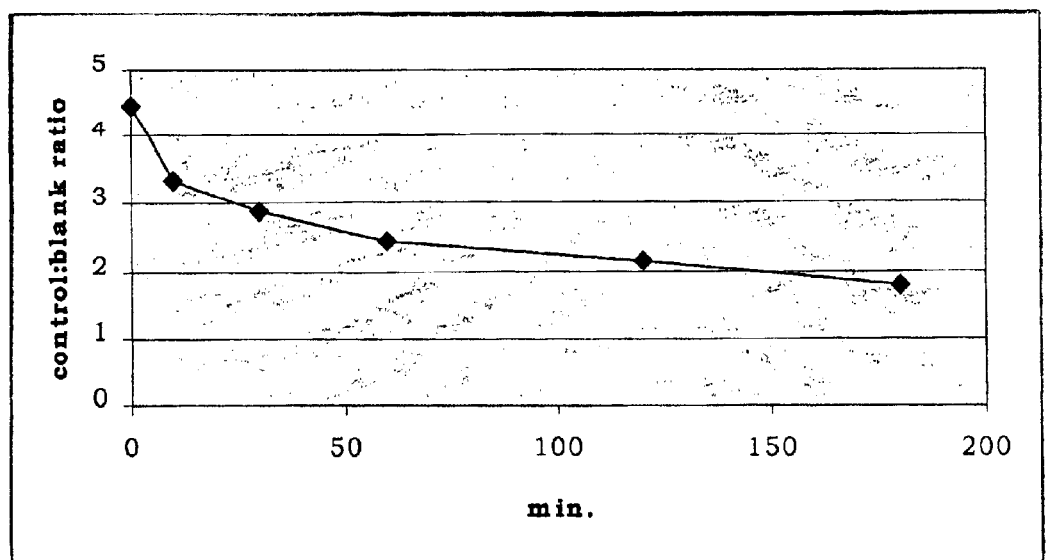

Incubation Time in Ammonium Molybdate Before Addition of CsCl:

The effect on cpm of varying the length of time between AmMo addition and CsCl addition is shown in FIG. 5A, and the effect on signal-to-background ratios is shown in FIG. 5B. It appears that the reaction signal is approximately constant, but the blank rises with time; thus signal to background decreases with increased incubation times.

Figure 6A:
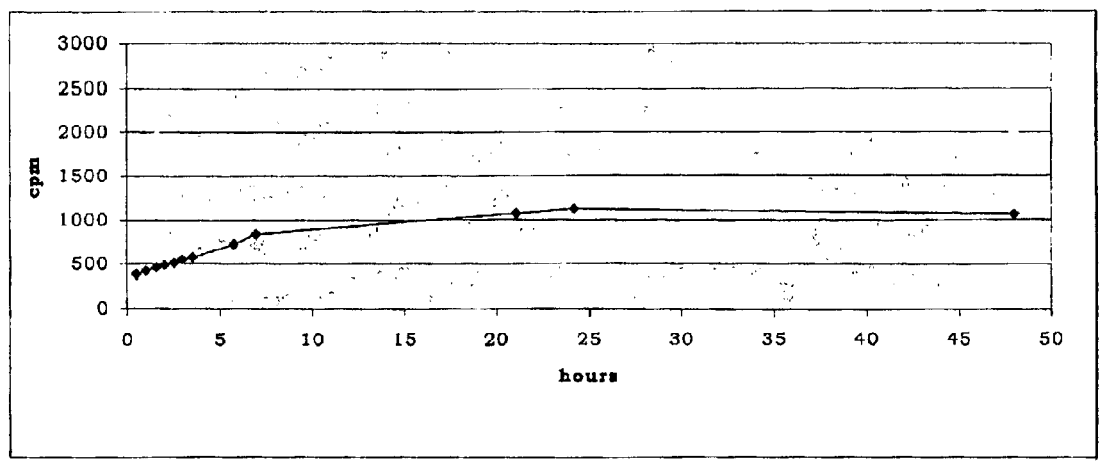
FIG. 6: The effect on SPA signal of varying the time the complete reaction mixture is incubated after addition of CsCl and prior to counting. (a) cpm for E1 reactions (squares) and blanks (diamonds). (b) control to blank ratio.
Figure 6B:
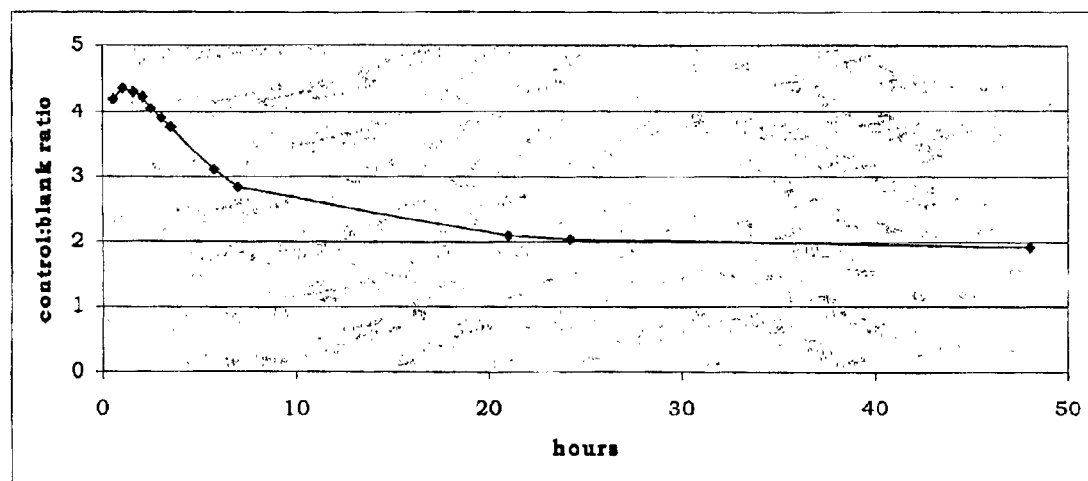

Time Between CsCl Addition and Scintillation Counting:

In the standard procedure, plates are counted one hour following addition of CsCl solution. The cpm and signal-to-noise ratios obtained by counting the same plate at various times over a 48-hour period are shown in FIGS. 6A and 6B.

Stability of Signal:

The experiments in FIGS. 5 and 6 indicate that the assay signal is unstable. The blank increases steadily with time. It was shown by TLC detection that mixing ATP and HCl at the concentrations above results in a slow degradation of ATP to phosphate, and this almost certainly accounts for the increase in signal observed. The same problem occurs in other assays which rely on phosphomolybdate formation to detect phosphate, for example by a change in color or the formation of a precipitate. It has been shown that citric acid, added immediately after AmMo, will tightly bind to any free molybdate, preventing the incorporation of subsequently released phosphate into phosphomolybdate anions. Exchange is extremely slow, so addition of citrate does not decrease the concentration of preformed phosphomolybdate, even after several days.

Figure 7:
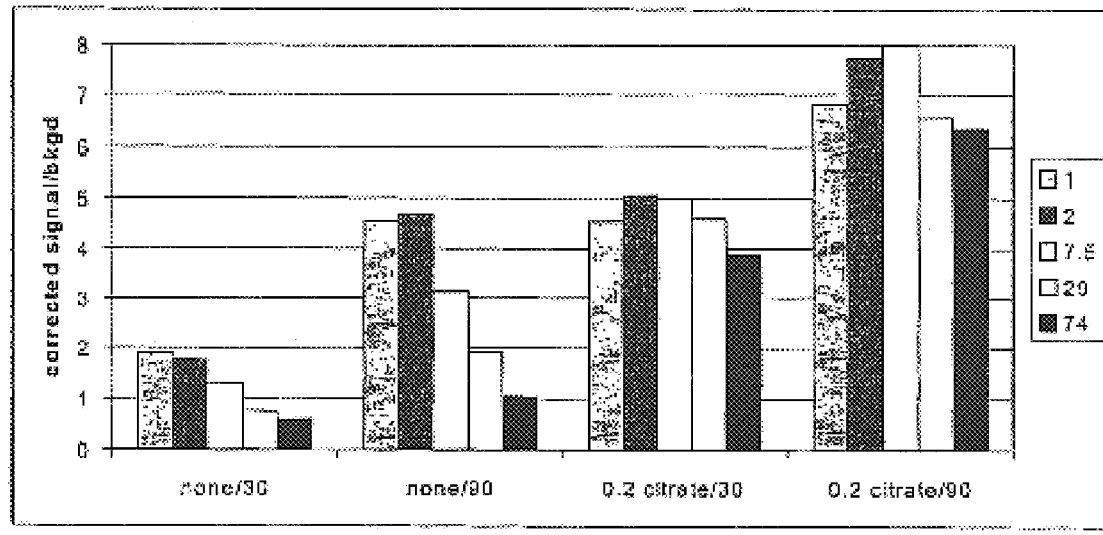
FIG. 7: The effect of CsCl volume and addition of citric acid to reaction on the E1 reaction: blank ratio. Results shown are for addition of 30 or 90 µL of CsCl with or without 0.2 M citric acid. The assay plate was read at times ranging from 1 to 74 hours after addition of CsCl.

The effect of adding 0.2 M citric acid to the 7M CsCl solution is shown in FIG. 7. In this experiment, 30 µL E1 ATPase reactions were run as described at the beginning of Example 3. After this, 30 µL of 2% AmMo in 1 M HCl was added followed immediately by 30 µL of 10 mg/mL SPA beads and then 30 or 90 µL of 7M CsCl±0.2 M citric acid. The signal is enhanced approximately two-fold after a one hour incubation, and is significantly stabilized by the addition of citric acid, so that little change is observed even after three days.

Figure 8:
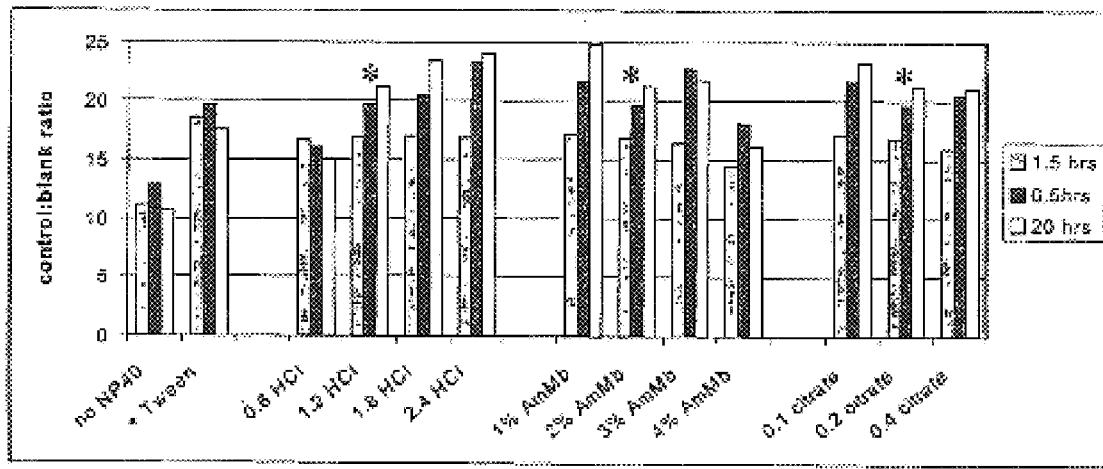
FIG. 8: The effect of HCl, AmMo, and citrate concentrations on the control: blank ratio. Results are shown for three different reading times after addition of CsCl. The marked results are for the preferred reagent concentrations. This marked combination is repeated three times to facilitate comparisons within each concentration series. As described in Example 3, the first two sets of results represent absence of Igepal-CA630 from reactions and addition of Tween-20 to the AmMo solution, respectively.

An additional experiment showing the effect of AmMo, CsCl, HCl, and citric acid concentrations on the signal and signal stability is shown in FIG. 8. Reactions were run as described at the beginning of this example except that the detergent Igepal-CA630 (Sigma, equivalent to Nonidet-P40) was present at 0.005% in all but one set of reactions, and citric acid was included in the CsCl solution at 0.1M, 0.2M or 0.4M. 0.05% Tween-20 was included in the ammonium molybdate solution in one case. Tween-20 is known to stabilize the phosphomolybdate-malachite green complex in the assay of Itaya and Ui (Clin Chim Acta, 1966), but has no beneficial effect in this assay. The assay plate was read at 1.5, 6.5, and 20 hours after addition of CsCl/citric acid. The signal increased only slightly after 1.5 hours and was stable up to at least 20 hours.

The control inhibitor ATP-γ-S was added to some wells at 10 µM (data not shown, but see example 4), to verify the robustness of the data obtained at the different time points. Over all conditions and time-points tested, the level of inhibition only varied from 63.9 to 70.0%. Thus the variations in detection under the different conditions of the assay may have an effect on observed cpm, but do not affect the relative signals between enzyme reactions, inhibited reactions, and blanks, and thus do not affect the fundamental accuracy of the assay.

Figure 9:
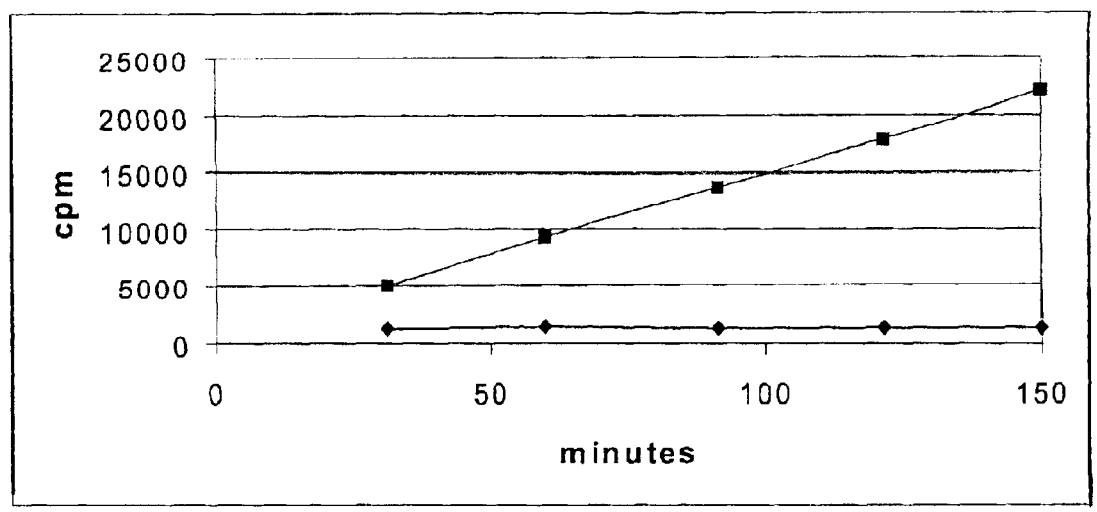
FIG. 9: Reaction time-course, as described at the end of Example 3. Shown are cpm for E1 reactions (squares) and blanks (diamonds).

An example of a time-course run using HPV-11 E1 is shown in FIG. 9. This experiment was run under the conditions described above for FIG. 8, except for the presence of 0.005% detergent as described above. Data shown are the averages for four 180 µL reactions. At each time-point, 30 µL was removed and mixed with 30 µL AmMo/SPA beads solution followed by 90 µL of 7.0 M CsCl/0.2 M citric acid prior to scintillation counting.

Example 4
Inhibition by ATP-γ-S

The following solutions were used to run 45 µL reactions for $IC_{50}$ curves:
ATP (15 µL per reaction), consisting of 3.0 µM ATP, 1.5 mM Mg acetate, and 0.06 µCi [γ-$^{33}$P]ATP;
E1 (15 µL per reaction), consisting of 18 nM HPV-6 E1;
inhibitor solution (15 µL per well) consisting of γ-S-ATP dissolved in buffer plus 18% DMSO.

Figure 10:
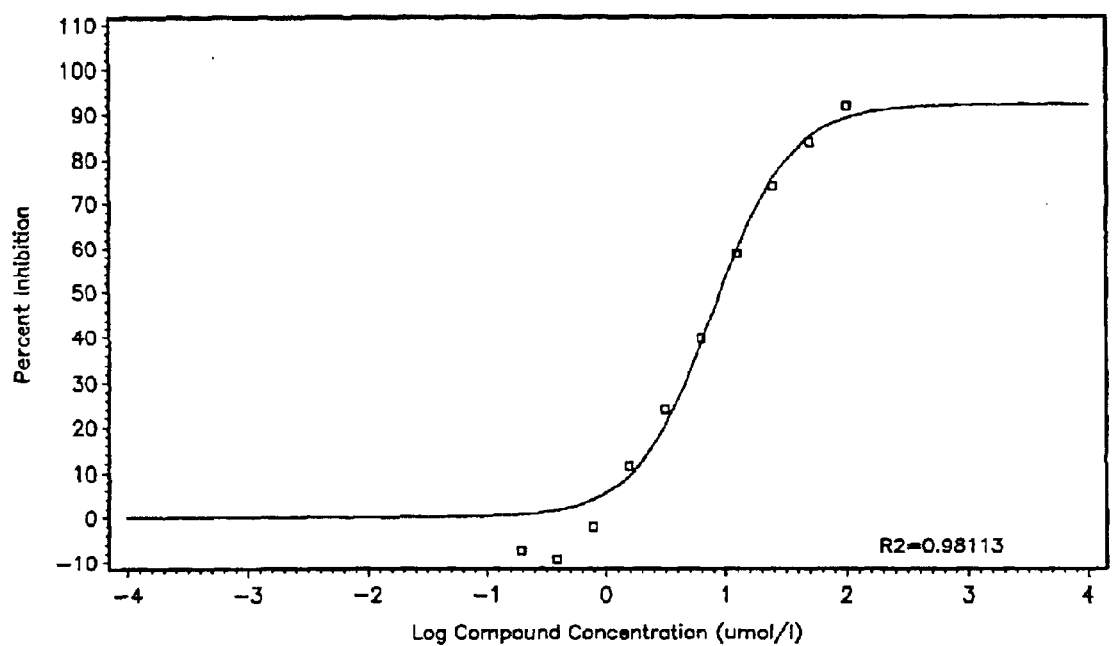
FIG. 10: $IC_{50}$ curve for inhibition of HPV-6a ATPase activity by ATP-γ-S. Nonlinear regression gave an $IC_{50}$ value of 8.0±1.6 µM.

All solutions are made in the assay buffer described in Example 3 except that the assay buffer also contained 0.005% Igepal CA-630. All components are diluted 3-fold on mixing the reactions. The reactants were added in the following order: a) inhibitor, b) HPV-6 E1, c) ATP. The concentration range for the inhibitor in the reactions was 0.2 to 100 µM. After 75 minutes, reactions were quenched by adding 45 µL of a mixture consisting of two parts streptavidin SPA bead (15 mg/mL suspension) in resuspension buffer (Example 2) and one part 2.4 M HCl containing 2% ammonium molybdate. Then 90 µL of 7 M CsCl containing 0.1 M citric acid was added. After mixing briefly, plates were left for 90 minutes and then counted on a TopCount. Inhibition data (see FIG. 10) were fit to a logistic using SAS (Statistical Software System; SAS Institute, Inc. Cary, N.C.) with positive controls averaging 16,000 cpm and blanks averaging 1300 cpm. Similar results have also been obtained in cases where detection was performed by TLC.

Example 5
Linearity and Accuracy of Phosphate Detection

Figure 11:
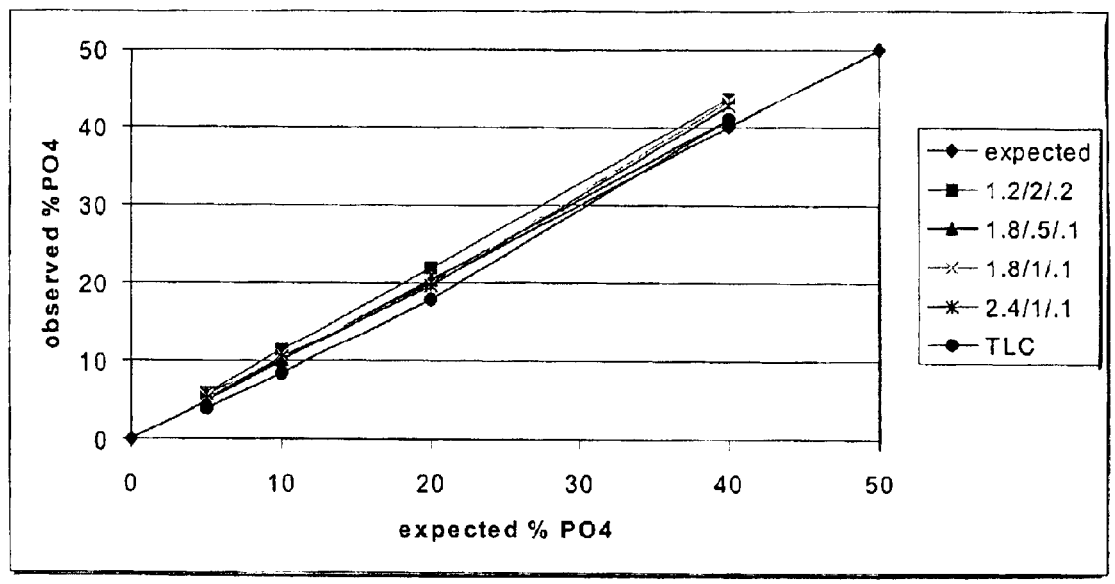
FIG. 11: Linearity and accuracy of phosphate detection. Lines shown are: theoretical reference (observed value= expected value, diamonds); SPA result using 1.2 M HCl, 2% AmMo, and 0.2 M citrate as described in example 5 (squares); SPA result using 1.8 M HCl, 0.5% AmMo, and 0.1 M citrate (triangles); SPA result using 1.8 M HCl, 1% AmMo, and 0.1 M citrate (crosses); SPA result using 2.4 M HCl, 1% AmMo, and 0.1 M citrate (asterisks); and TLC result (circles).

In this experiment, one large ATPase reaction was run with sufficient E1 to give 100% ATP hydrolysis. The E1 was then heat-inactivated, and the reaction mixture was mixed in various proportions with a reaction blank containing no E1. Reaction buffer and incubation conditions were as described in example 1 except that the reaction buffer was as described in example 3, though 0.005% Igepal-CA630 was present. Reaction-blank mixtures were made at 2:3, 1:5, 1:10, and 1:20 to simulate a range from 40% to 5% hydrolysis. As for some of the experiments above, SPA detection was performed using ammonium molybdate, HCl, and citric acid at several different concentrations. Results for some conditions, along with those for TLC, are shown in FIG. 11. In all cases, the signal detected (expressed as proportion of 100% for SPA and as the observed phosphate concentration for TLC) are very similar. Although the absolute signal (cpm) varies with conditions, the relative signal and thus the accuracy of the assay is constant. In particular, 20% conversion simulates a typical extent of reaction under screening conditions and 10% conversion represents the signal which would be observed for test compounds giving 50% inhibition.

Example 6
Variation for Assay Controls Under Screening Conditions

Figure 12:
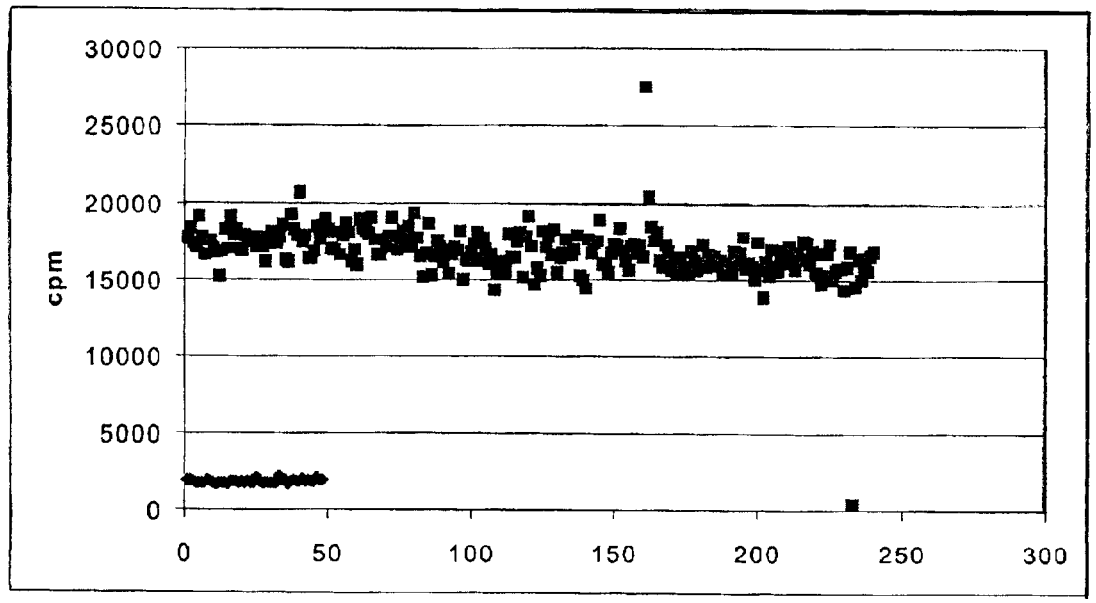
FIG. 12: Signal obtained for E1 reactions (squares) and blanks (diamonds) run on three separate plates. The x-axis is the well number, an arbitrary scale to spread the data for viewing.

To verify the well-to-well variability of this method, reactions were run as described in example 1 in 80 wells of three separate 96-well plates. Reaction blanks without enzyme were run in the other 16 wells. Results are shown in FIG. 12. Well-to-well variability can be measured through the z' statistic, which takes into account standard deviations of the signals and the separation between the signal from enzymatic reactions and blanks (J-H Zhang, et al, J. Biomol. Screening, 1999, 4, 67–73). Values can range from less than 0 to 1.0, with values greater than 0.5 deemed very acceptable for a screening assay. The z' value for this experiment was 0.63 or 0.75 when two clear outliers were removed from the analysis.

Example 7
Linearity of Phosphate Detection at Higher Phosphate Concentrations

The Examples above demonstrate that SPA detection of phosphate works well for low concentrations of phosphate, 0.1–1 µM. However, in order to carry out mechanistic work, it is necessary to vary the ATP concentration more widely. We had observed that the procedure outlined in Example 1 did not quantitatively capture all orthophosphate, since increased signal was observed if larger amounts of SPA beads were added. Based on those initial results, an SPA bead titration experiment was carried out as described below.

Similarly to Example 5, for this experiment one larger reaction was run using a high concentration of E1. In this case, the ATP concentration was 200 µM. The reaction was run for four hours at room temperature and then for two hours at 37° C. to ensure complete conversion. A sample was analyzed by TLC to verify quantitative conversion. The reaction was then serially diluted with reaction buffer plus magnesium to give a range from 200 μM to 0.2 μM phosphate concentrations. Samples were analyzed by combining 45 μL of diluted reaction with 15 μL of ammonium molybdate (2% in 2.4 M HCl) and 30 μL of SPA bead suspension at 7.5, 15, 30, or 60 mg/mL. Finally 90 μL of 7M CsCl plus 0.2 M citric acid was added to all wells.

Figure 13A:
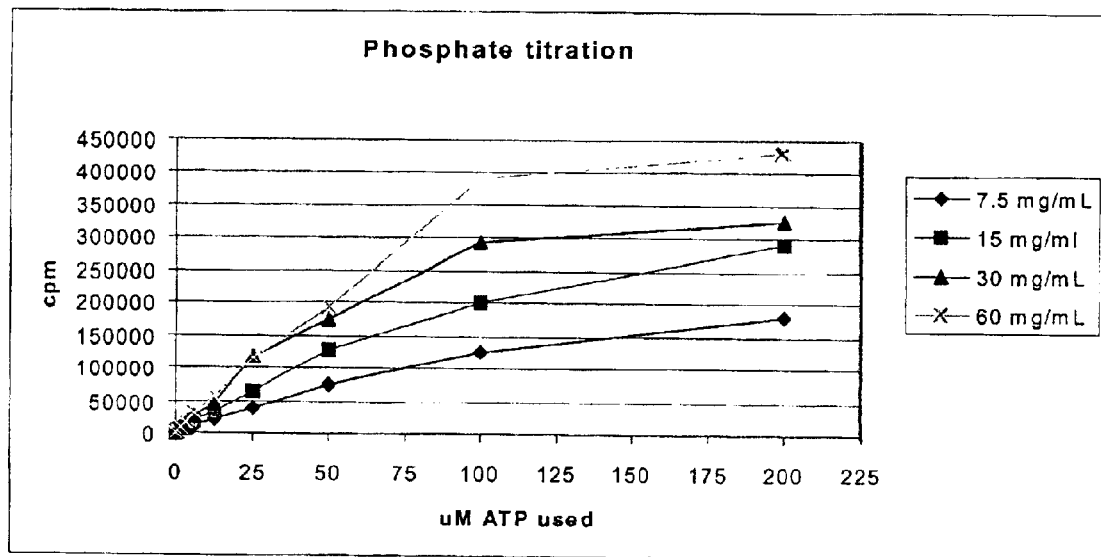
FIG. 13: SPA signal obtained for 0.2 to 200 µM phosphate. Results are shown for four different SPA bead concentrations. (a) linear scale (b) logarithmic scale. The theoretical line shown in (b) (asterisks) is simply a straight line for reference.
Figure 13B:
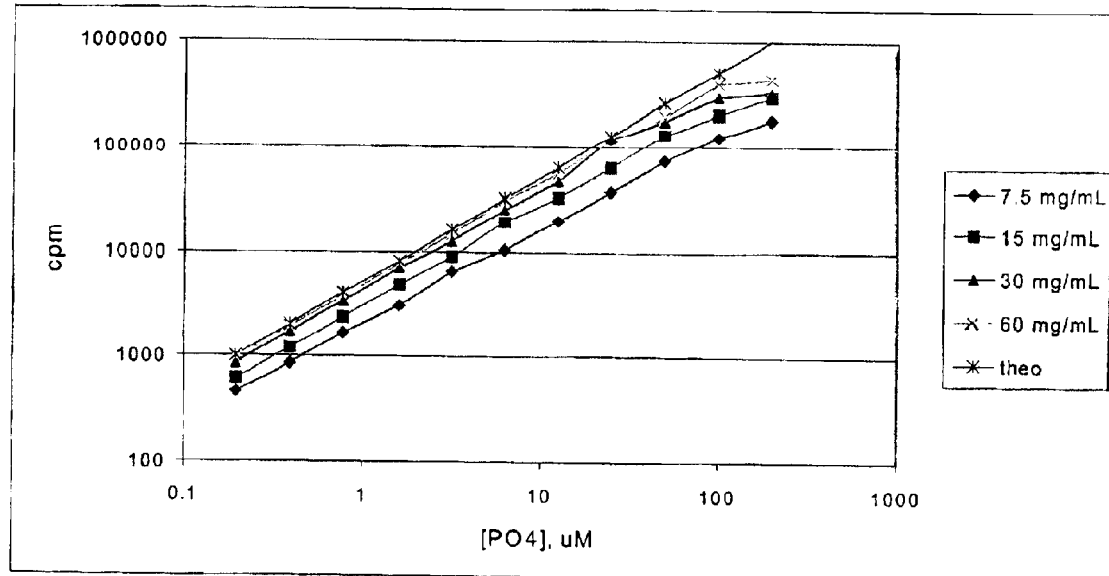

Results are shown in FIG. 13A and as a log-log plot in FIG. 13B. As seen most clearly in FIG. 13B, for each SPA bead concentration the signal was directly proportional to the phosphate concentration up to about 100 μM. However, the absolute signal does depend on the bead concentration. Interestingly, the lines in FIG. 13B are parallel, i.e. the proportional increase in signal obtained by increasing the SPA bead concentration is the same at all phosphate concentrations, up to about 100 μM.

Example 8

Figure 14A:
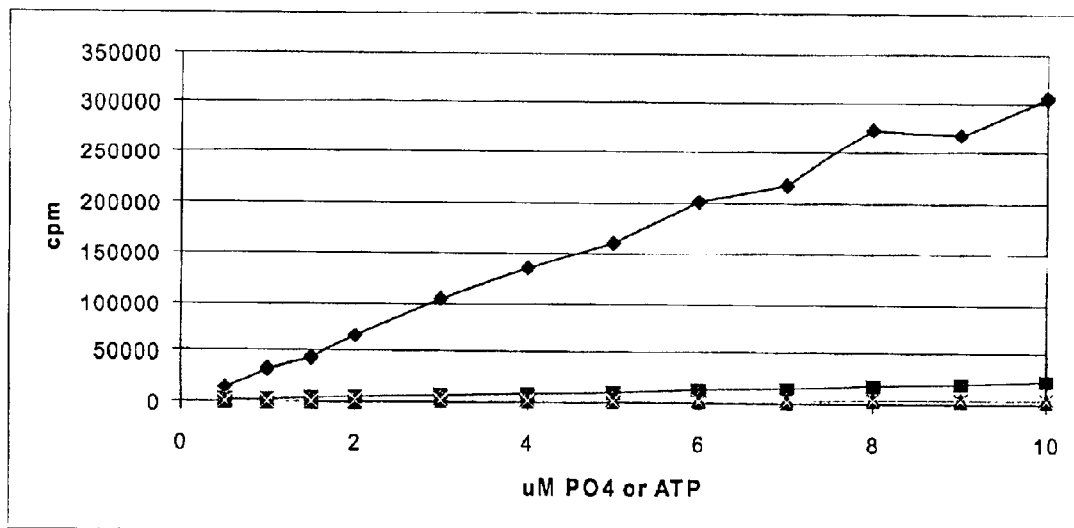
FIG. 14: SPA signal obtained for 0.5 to 10 µM phosphate or ATP. Results are shown for phosphate in the presence of AmMo (diamonds); phosphate in the absence of AmMo (triangles); ATP in the presence of AmMo (squares); and ATP in the absence of AmMo (crosses). (a) linear scale (b) logarithmic scale.
Figure 14B:
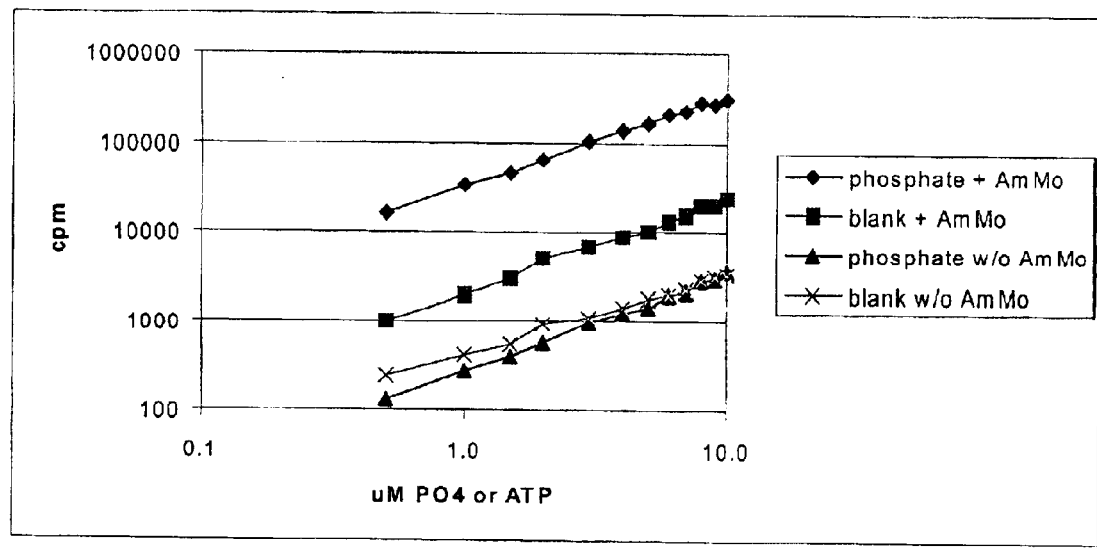

Titration of ATP and Phosphate in the Presence and Absence of AmMo in Order to Determine the Source of Signal in the Absence of Enzyme In this experiment, a large reaction similar to the one above was run to completely convert 10 μM ATP to phosphate and ADP; complete conversion was verified by TLC (Example 2). In parallel, an identical mixture lacking enzyme was produced. Each was diluted in buffer as above to give solutions with phosphate or ATP concentrations ranging from 10 μM to 0.5 μM. Duplicate 45 μL samples of each were mixed with either 40 μL of AmMo/SPA bead mixture as described in Example 1 or with a similar mixture lacking AmMo (but still containing HCl), followed by 80 μL of CsCl/citric acid. Results are graphed in FIG. 14A or as a log-log plot in FIG. 14B. As expected, based on Example 7, the signal is linearly dependent on the radioactivity concentration in all cases. In the presence of AmMo, the reaction blank (ATP solution) gives a signal equal to approximately 5% of the phosphate solution produced by total conversion. Unlike the experiment in Example 3 (FIG. 2), most of the blank signal is dependent on AmMo, and thus under these conditions, the blank is primarily due to contaminating orthophosphate already present in the commercial ATP solution.

Example 9

Value of $K_m$ (ATP) for HPV-11 as Determined by SPA and TLC Methods

ATPase time-courses were run at different concentrations of ATP in order to determine the kinetic parameter $K_m$(ATP) for HPV-11 E1. Reactions were run under similar conditions in both experiments, using the procedures given in Examples 1 and 2, except that the concentration of Igepal-CA630 was 0.01% rather than 0.005% and with experiment-specific changes noted below. The E1 concentration was 2 nM and the ATP concentrations ranged from 3–75 μM (TLC) or 2–50 μM (SPA), with the MgOAc concentration equal to the ATP concentration plus 0.5 mM. Stock solutions of ATP at each concentration were obtained by diluting the highest concentration solution with buffer containing 0.5 mM MgOAc; thus a constant ratio of radiolabeled to unlabeled ATP was used for all reactions. Reaction rates were measured by taking time-points from 10 or 20 to 120 minutes. To insure initial velocity conditions, time-points giving greater than 20% conversion were not used for analysis.

Detection and Data Processing for the SPA $K_m$ Experiment:

Total reaction volumes were 150 μL. For each time-point, 20 μL of reaction mixture was removed and combined with 40 μL of ammonium molybdate/SPA bead mixture followed by 80 μL of CsCl/citric acid. All reactions were run in triplicate. Plates were counted after overnight incubation. At the last time-point, an additional 20 μL aliquot was removed and combined with 10 μL 0.5 M EDTA. In this case, the conversion of ATP to phosphate was quantified by TLC, and the concentration of phosphate determined by TLC was compared to the cpm from the SPA procedure, after subtraction of blanks in both cases. The relationship between phosphate concentration and cpm is linear and the slope of the line was used to convert cpm values from SPA detection to concentration of phosphate produced. Rates of phosphate production at each ATP concentration were fit by nonlinear regression to the Michaelis-Menten equation using the program Grafit (V 3.01, R. Leatherbarrow). Results are shown in FIG. 15.

Detection and Data Processing for the TLC $K_m$ Experiment:

As for the SPA experiment above, 150 μL reactions were run, in duplicate. At each time-point, 20 μL were removed and combined with 10 μL of ice-cold 0.5 M EDTA. At the completion of the time-course, reactions were diluted such that the total radioactivity concentration for each point was approximately equal. Thus reactions at 75 μM ATP were diluted 25-fold whereas 3 μM ATP reactions were not diluted. The dilution buffer consisted of two parts reaction buffer containing 500 μM magnesium acetate and one part 0.5 M EDTA. One μL of each diluted reaction was spotted for TLC detection. The values for percent conversion of ATP to phosphate were determined as described in Example 2 and these were used to determine reaction rates at each ATP concentration. These rates were then fit to the Michaelis-Menten equation as described above to give an estimate for the value of $K_m$(ATP) (FIG. 16).

Figure 15:
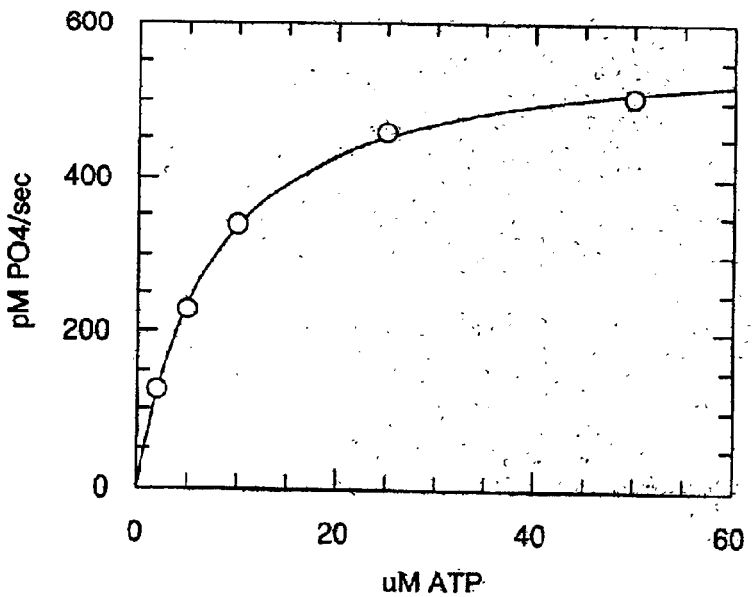
FIG. 15: Estimation of the value of $K_m$(ATP) for HPV-11 E1 determined by SPA detection. Experimentally determined values are represented as circles, the line represents the calculated theoretical best-fit for the Michaelis-Menten equation.
Figure 16:
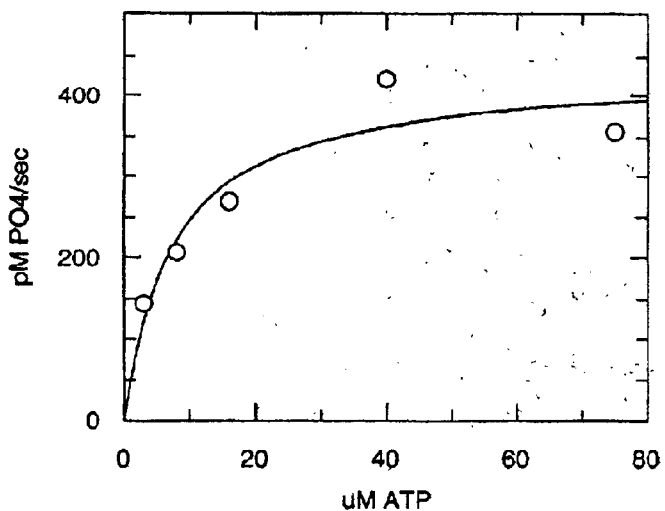
FIG. 16: Estimation of the value of $K_m$(ATP) for HPV-11 E1 determined by TLC detection. Experimentally determined values are represented as circles, the line represents the calculated theoretical best-fit for the Michaelis-Menten equation.

Comparison of FIGS. 15 and 16 clearly shows that the two techniques give similar results, but also that the quality of data is superior for the SPA method. Furthermore, the SPA method requires significantly less manipulation and shorter data processing time. Results shown are typical examples, each has been reproduced multiple times.

Example 10

Value of $K_i$(ATP-γ-S) for HPV-11 as Determined by the SPA Methods

Figure 17A:
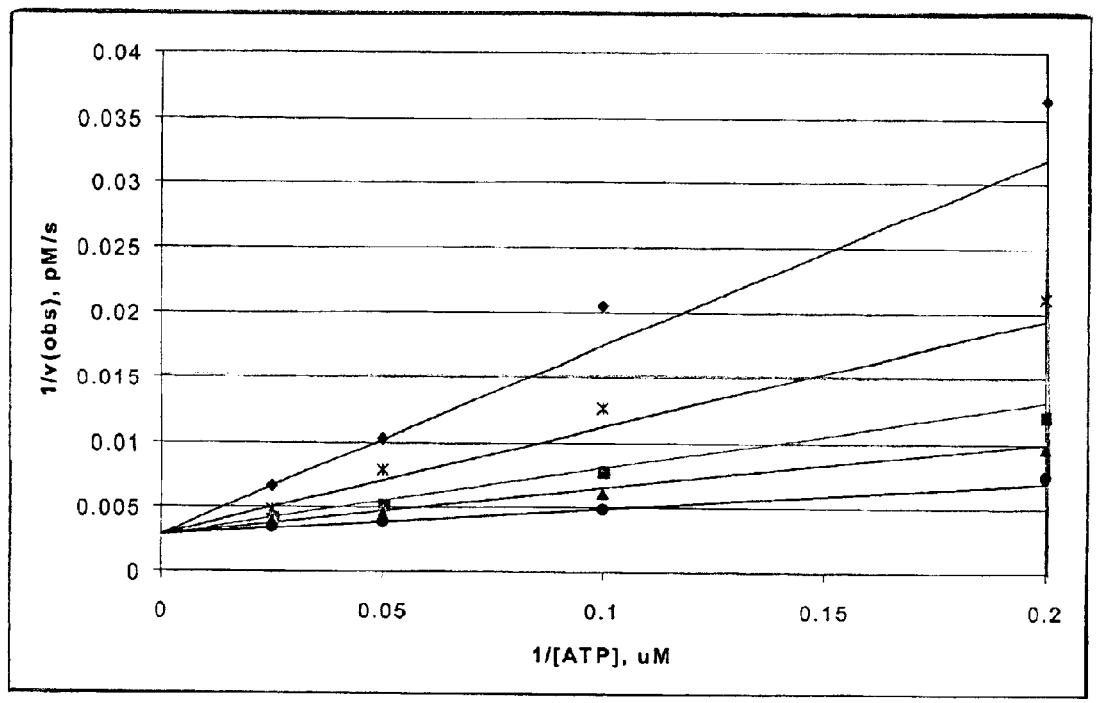
FIG. 17: Lineweaver-Burke (double reciprocal) plots comparing experimental inhibition data to theoretical results based on parameters obtained by nonlinear regression. (A) competitive inhibition model. (B) noncompetitive inhibition model (equal binding to E and ES). For both graphs, experimental values are given as points with inhibitor concentrations of 24 µM (diamonds); 12 µM (asterisks); 6 µM (squares); 3 µM (triangles); and 0 (circles). Lines are based on the best-fit parameters for each inhibition model.
Figure 17B:
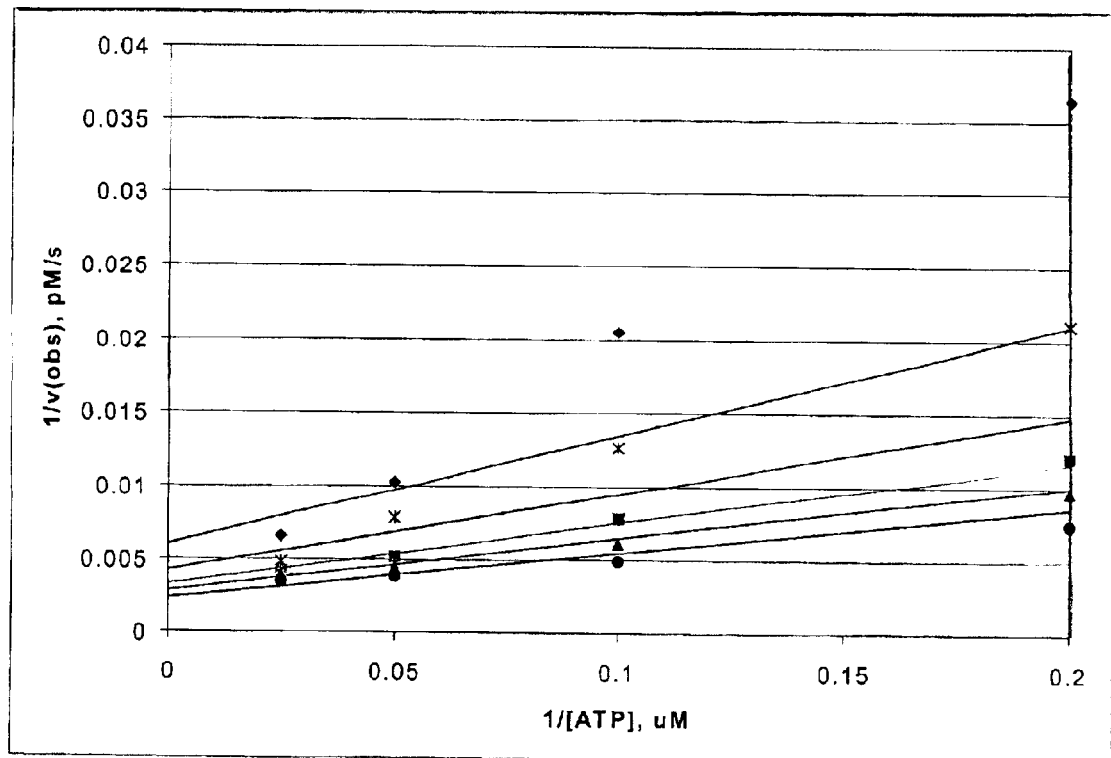

The γ-thio phosphate analog of ATP inhibits many ATPases by a competitive mechanism. Experimental determination of the mechanism of inhibitor action requires measuring initial velocities for a number of substrate and inhibitor concentrations. The number of data points needed (several hundred) and the precision required for this experiment mean that performing the experiment by TLC detection is much more difficult and tedious. The SPA procedure works well, however. For this experiment, ATP concentrations of 5, 10, 20 and 40 μM were used, along with inhibitor concentrations of 0, 3, 6, 12 and 24 μM. Reactions were run as described for Example 9 (SPA detection). Data were processed as above and fit by nonlinear regression to an equation for competitive inhibition using GraFit. We obtained values for $K_m$(ATP-γ-S) of 3.8±0.4 μM and for $K_m$(ATP) of 6.7±0.7 μM. A Lineweaver-Burke plot illustrating the fitness is shown in FIG. 17A. The plot was generated in Excel using the fitted parameters for the lines and the experimental values for points. For comparison, the data were also fit to an equation for non-competitive inhibition (equal binding of inhibitor to enzyme and enzyme-substrate complexes). Values obtained were 16±2 PM for $K_i$(ATP-γ-S) and 12±2 μM for $K_m$(ATP). The corresponding double reciprocal plot is shown in FIG. 17B. Because of the quality of the data obtained it is possible to observe a systematic deviation between the experimental and fitted values for this second mechanism, especially at higher inhibitor concentrations. A similar conclusion can be drawn from the significantly lower reduced chi squared value for the competitive fit compared to the noncompetitive fit (62 and 347 respectively). Thus as expected, the competitive model is more appropriate for this inhibitor.

Discussion

The procedure presented above is a sensitive, accurate, and robust method for the detection of orthophosphate produced by the cleavage of radiolabeled phosphate-containing compounds. It is highly suited to the task of measuring the activity of enzymes for which orthophosphate is a reaction product, and to measuring the inhibition of such activities. There are many such enzymes; common examples are helicases, ATPases and phosphatases. It is particularly appropriate for cases in which only low concentrations of orthophosphate (nM or low pM) are produced. Important cases will be those enzymes, such as the E1 helicase of HPV, which bind the phospho substrate tightly. This procedure allows assays to be run at substrate concentrations below the value of $K_m$ for maximum sensitivity to competitive inhibitors. The method is simple and robust enough for large scale inhibitor screening. In particular, the method is not sensitive to many common artifacts, for example apparent inhibition caused by colored or fluorescent compounds, and the signal produced is stable, reproducible, and relatively insensitive to small fluctuations in concentrations or volumes of assay components. The method is also accurate enough to be applied to quantitative enzymology studies. Other methods to detect orthophosphate have been discussed in the literature. Two widely reported methods use radiolabeled ATP to measure ATPase activity. Both of these methods involve the physical separation of products (e.g. ADP and Pi) from the starting material, using either TLC on PEI cellulose or selective adsorption of ATP onto charcoal. While sensitive enough to detect very low concentrations of orthophosphate, these are classical methods which cannot be easily adapted to modern screening applications. Other assay methods rely on coupling enzymes which use orthophosphate (or another reaction product) as the substrate in a second reaction, producing an absorbance or fluorescence change. These can be quite accurate, but are less sensitive than radioactivity-based assays. Furthermore, the addition of a coupling enzyme complicates the interpretation of results, since coupled-enzyme assays are subject to additional artifacts. Several other procedures involve formation of phosphomolybdate followed by reduction or dye absorption to produce a color change, which can be correlated with phosphate concentration. Some enzyme assays based on these procedures are accurate and robust enough to be used in compound screening efforts or enzymology studies, but it is not practical to use these methods to detect low $\mu$M or nM concentrations of orthophosphate. In some applications, it is possible to enhance the sensitivity of these methods by concentrating large volumes of dilute phosphomolybdate onto Sephadex or related resins. This has not proved applicable to screening applications, however, since only very small volumes are normally used in each test reaction. It has been shown that one can selectively adsorb radiolabeled phosphate onto the surface of polyvinylpolypyrrolidone (PVPP). Radiolabeled ATP or other contaminants can then be washed away and the remaining phosphate detected by elution at elevated pH. This specific procedure is not very practical for enzymatic studies, since it requires the physical separation of reactants and products, and the reproducibility, which is dependent on elution of multiple samples from PVPP columns, would be relatively poor. The authors suggest that an important component of the selectivity of their procedure is the ability of polyvinylpyrrolidone to catalyze the formation of phosphomolybdate, thereby implying that other hydrophobic surfaces would be less suited to their method, thus leading away from the present invention.

What is claimed is:

1. A method for determining ATPase activity, comprising the steps of:
    a. mixing radiolabeled [$\gamma$-$^{33}$P]ATP with an ATP hydrolyzing enzyme to form a reaction mixture;
    b. incubating the reaction mixture for a sufficient time to afford orthophosphate to be released from hydrolysis;
    c. adding a solution of molybdate to said reaction mixture to form a phosphomolybdate complex;
    d. contacting said phosphomolybdate complex with a scintillant hydrophobic surface; and
    e. measuring scintillation of said scintillant as a means to calculate the amount of said orthophosphate,
    wherein release of orthophosphate correlates to ATPase activity.

2. The method according to claim 1, wherein said ATP hydrolyzing enzyme is an E1 helicase protein from human papillomavirus.

3. The method according to claim 1, wherein said solution of molybdate and hydrophobic surface are added simultaneously to said reaction mixture.

4. The method according to claim 1 further comprising the step of:
    f. adding a solution of CsCl to said reaction mixture prior to measuring scintillation.

5. The method according to claim 4, further comprising the step of:
    g. adding a solution of citric acid to said reaction mixture prior to measuring scintillation.

6. The method according to claim 5, wherein said CsCl and citric acid are added simultaneously to the reaction mixture.

7. The method according to claim 5, wherein said citric acid is at a final concentration ranging from 0.05 to 0.2M.

8. The method according to claim 7, wherein said citric acid is at a final concentration of about 0.1M.

9. The method according to claim 4, wherein said CsCl is at a final concentration higher than 1M.

10. The method according to claim 9, wherein said CsCl is at a final concentration ranging from 2M to 4M.

11. The method according to claim 10, wherein said CsCl is at a final concentration of about 3.5M.

12. The method according to claim 1, wherein said molybdate is at a final concentration of from 0.05% to 0.3% w/v.

13. The method according to claim 12, wherein said molybdate is at a final concentration of from 0.1% to 0.2% w/v.

14. The method according to claim 13, wherein said molybdate is at a final concentration of about 0.17% w/v.

15. The method according to claim 1, wherein said hydrophobic surface is selected from the group consisting of: polyvinyltoluene (PVT), alpha-dextran, latex, polystyrene, polyacrylamide, acrylamide, agarose, polypropylene, polycarbonate, and 3,6-anhydro-alpha-L-galacto-beta-D-galactan.

16. The method according to claim 15, wherein said hydrophobic surface is polyvinyl toluene beads.

17. A method for screening inhibitors of a phosphate-hydrolyzing enzyme activity comprising the steps of:

i. determining ATPase activity according to claim 1 in the absence of a candidate inhibitor.

ii. determining ATPase activity according to claim 1 wherein a candidate inhibitor is added at step a, iii. comparing the amount of orthophosphate released in step i to the amount of orthophosphate released in step ii, wherein a lesser amount of orthophosphate released in step ii compared to the amount of orthophosphate released in step i indicates the candidate is an inhibitor of phosphate-hydrolyzing enzyme activity.

18. A method for screening inhibitors of a phosphate-hydrolyzing enzyme activity comprising the steps of:

i. determining ATPase activity according to claim 5 in the absence of a candidate inhibitor, ii. determining ATPase activity according to claim 5 wherein a candidate inhibitor is added at step a, iii. comparing the amount of orthophosphate released in step i to the amount of orthophosphate released in step ii, wherein a lesser amount of orthophosphate released in step ii compared to the amount of orthophosphate released in step i indicates the candidate is an inhibitor of phosphate-hydrolyzing enzyme activity.

19. The method according to claim 18, wherein said phosphate-hydrolyzing enzyme is selected from the group consisting of helicase, ATPase, and phosphatase.

20. The method according to claim 19, wherein said phosphate-hydrolyzing enzyme is an ATPase.

21. The method according to claim 20, wherein said ATPase is an E1 helicase from human papillomavirus.

* * * * *